(12) United States Patent
Chaudhuri

(10) Patent No.: US 7,166,273 B2
(45) Date of Patent: *Jan. 23, 2007

(54) PHOTO STABLE ORGANIC SUNSCREEN COMPOSITIONS

(75) Inventor: Ratan K. Chaudhuri, Lincoln Park, NJ (US)

(73) Assignee: EMD Chemicals, Inc., Hawthorne, NY (US)

( * ) Notice: Subject to any disclaimer, the term of this patent is extended or adjusted under 35 U.S.C. 154(b) by 667 days.

This patent is subject to a terminal disclaimer.

(21) Appl. No.: 10/452,199

(22) Filed: Jun. 3, 2003

(65) Prior Publication Data

US 2004/0247536 A1   Dec. 9, 2004

(51) Int. Cl.
*A61Q 17/00* (2006.01)
*A61Q 17/04* (2006.01)
*A61Q 19/00* (2006.01)
*A61K 8/00* (2006.01)

(52) U.S. Cl. .......................... 424/59; 424/60; 424/400; 424/401

(58) Field of Classification Search .................. 424/59, 424/60, 400, 401
See application file for complete search history.

(56) References Cited

U.S. PATENT DOCUMENTS

| 6,238,650 | B1 | 5/2001 | Lapidot et al. |
| 6,436,375 | B1 | 8/2002 | Lapidot et al. |
| 6,468,509 | B1 * | 10/2002 | Lapidot et al. ............... 424/59 |
| 6,602,515 | B1 * | 8/2003 | Chaudhuri .................. 424/401 |
| 6,831,191 | B1 * | 12/2004 | Chaudhuri .................. 560/105 |
| 2002/0104122 | A1 | 8/2002 | Kakitani et al. |
| 2003/0108492 | A1 | 6/2003 | Chaudhuri |

FOREIGN PATENT DOCUMENTS

| WO | WO 0071084 | 11/2000 |
| WO | WO 0072806 | 12/2000 |
| WO | WO 0124762 | 4/2001 |
| WO | WO 03007906 | 1/2003 |

* cited by examiner

*Primary Examiner*—Shelley A Dodson

(57) ABSTRACT

Photostable broad-spectrum organic sunscreen compositions comprising a UV-A sunscreen, such as Avobenzone, a photostabilizer, a UV-B liquid organic sunscreen, and a solubilizer and further enhancing the photostability by encapsulation using a sol-gel process.

136 Claims, 3 Drawing Sheets

PHOTO STABLE ORGANIC SUNSCREEN COMPOSITIONS

This application is related to applicant's application Ser. Nos. 09/904,904 (filed Jul. 16, 2001) and 10,022,343 (filed Dec. 20, 2001).

BACKGROUND OF THE INVENTION

Topical sunscreen compositions are commonly used during outdoor work or leisure as a means for providing protection of exposed skin against acute and chronic adverse effects of solar radiation such as, for example, sunburn, cancer and photo-aging. Many effective sunscreen preparations are sold commercially or are described in cosmetic or pharmaceutical literature. In general, sunscreen preparations are formulated as creams, lotions or oils containing as the active agent an ultra violet radiation absorbing chemical compound. The sunscreen functions by blocking passage of ultra violet radiation thereby preventing its penetration into the skin.

According to Zecchino et al. (U.S. Pat. No. 5,008,100), sunscreen agents may be characterized in the order of decreasing effectiveness as either highly chromophoric (monomeric organic compounds and inorganic compounds such as titanium dioxide) and minimally chromophoric (polymeric organic solids).

Organic sunscreens are classified into UV-A filters, UV-B filters or broad spectrum filters (UV-A and UV-B functionality in a single molecule) depending on the type of radiation they absorb. UV-A sunscreens absorb radiation in the 320 to 400 nm regions of the ultra violet spectrum and UV-B sunscreens absorb radiation in the 290 to 320 nm regions of the ultra violet spectrum.

Broad band sunscreens (UV-A and UV-B functionality) absorb radiation in the 290 to 400 nm region of the ultra violet spectrum and have two maximums, one in the UV-B region and the other in the UV-A region.

Representative references related to UV sunscreens are:

U.S. Pat. No. 3,278,448, which discloses cinnamic acid derivatives such as 4-hydroxy, 3–5-ditertbutyl-alphacarbethoxy-cinnamic acid ether ester in column 2, line 20;

U.S. Pat. No. 3,538,226, which describes cinnamic acid alkyl ester derivatives at column 1, lines 15–31 and column 2, lines 1–12 and column 3, lines 30–55 and 60;

U.S. Pat. No. 5,175,340, which describes cinnamic acid alkyl esters having hydroxy radicals and alkoxy radicals on the phenyl ring, and U.S. Pat. No. 5,830,441, which describes UV absorbents containing a cyano or cinnamyl moiety by the generic formula at col. 2, lines 1–21.

Other references which disclose cinnamide compounds include U.S. Pat. Nos. 5,601,811, 4,335,054, 5,124,354, 5,294,643 and 5,514,711.

Unfortunately, some of the highly chromophoric monomeric organic compounds employed in sunscreen compositions are not photostable and the protection from sun damage is lost. For example, Avobenzone, a UV-A sunscreen, is generally photo-unstable. Furthermore, photo-instability of Avobenzone increases significantly when combined with Octyl methoxycinnamate (UV-B organic sunscreen). In most studies, Octyl methoxycinnamte (OMC) has been regarded as relatively photostable. The absorption maxima of Avobenzone (~360 nm) and OMC (~310 nm) do not overlap sufficiently to allow directly excited singlet—singlet energy transfer to occur. However, transfer from one excited triplet-state to another is possible provided the energy levels are suitable.

The triplet-state of OMC has been shown to quench the triplet-states of 8-methoxy psoralen and 5-methoxy psoralen, subsequently undergoing E/Z isomerization (Morliere P., O. Avice, T. S. Melo, L. Dubertret, M. Giraud and R. Santus, A study of the photochemical properties of some cinnamte sunscreens by steady state and flash photolysis. Photochem. Photobiol, 36, 395–399 (1982); Morliere P., G. Huppe, D. Averbeck, A. R. Young, R. Santus, and L. Dubertret, In-vitro photostability and photosensitizing properties of bergamot oil. Effects of a cinnamte sunscreen. J. Photochem. Photobiol. B, Biol, 7, 199–208 (1990)). This is clearly evident that the triplet state of OMC is accessible to triplet energy transfer and that subsequent chemistry occurs.

The triplet-state of Avobenzone is surprisingly accessible and allowing energy transfer to other nearby molecules having triplet states with suitable overlap; the presence of OMC provides a suitable target acceptor. OMC undergoes E/Z photoisomerization upon accepting triplet state energy transfer and subsequent photolysis of OMC. It would appear that photo-instability of Avobenzone may cause the photolysis of OMC when they are combined together. This limits obtaining a broad-spectrum (UV-A and UV-B) sunscreen composition combining Avobenzone with Octyl methoxycinnamte.

In addition to lack of photostability of many organic sunscreens, they do not possess an antioxidant property, which protects skin or hair.

The ideal sunscreen formulation/composition should be nontoxic and non-irritating to the skin tissue and be capable of convenient application in a uniform continuous film. The product should be chemically and physically stable so as to provide an acceptable shelf life upon storage. It is particularly desirable that the preparation should retain its protective effect over a prolonged period after application. Thus, the active agent when present on the skin must be resistant to chemical and/or photo degradation.

Techniques for stabilizing UV absorbent compositions are known. Representative disclosures in this area include U.S. Pat. Nos. 5,567,418; 5,538,716; 5,951,968 and 5,670,140.

Antioxidants are believed to function by providing protection from free-radical damage. To be an effective quencher, it is believed the antioxidant must be present in an adequate concentration at the site of free radical generation. Since antioxidants are used in low concentrations and are a separate ingredient, they may not be available at the site of generation, thereby reducing the desired level of skin protection. Based on these drawbacks, it is desirable to provide a photostable sunscreen composition wherein a photostabilizer having an antioxidant and sunscreen functionality in a single molecule is present to enhance the effectiveness of the protection of skin against sun damage.

SUMMARY OF THE INVENTION

Thus, the present invention relates to a photo-stable sunscreen composition comprising (a1) at least one UV-A organic sunscreen and (b) at least one photostabilizer, with optionally (a2) at least one UV-B liquid organic sunscreen and/or (c) at least one solubilizer, and/or (d) at least one cosmetically or pharmaceutically acceptable carrier. The preferred composition comprises (a1), (a2), (b), (c) and (d).

In a particular embodiment, the present invention relates to a photostable sunscreen composition comprising at least one UV-A organic sunscreen which belongs to the class of dibenzoylmethane or a derivative thereof; at least one photostabilizer belonging to the class of dialkylbenzalmalonate or a derivative thereof; at least one UV-B liquid organic sunscreen belonging to the class of salicylates or cinnamates or a combination thereof; at least one solubilizer which is an ester, a long chain fatty acid or an alcohol; and at least one cosmetically or pharmaceutically acceptable carrier.

For increasing the photostability, the sunscreen compositions of the invention are preferably prepared via a sol-gel encapsulation process as described in U.S. Pat. Nos. 6,468,509; 6,436,375; and 6,238,650.

Exemplary dibenzoylmethane derivatives according to the present invention include but are not limited to 2-Methyldibenzoylmethane, 4-Methyldibenzoylmethane, 4-Isopropyldibenzoylmethane, 4-Tert-butyldibenzoylmethane, 2,4-Dimethyldibenzoylmethane, 2,5-Dimethyldibenzoylmethane, 4,4'-Diisopropyldibenzoylmethane, 4,4'-Dimethyldibenzoylmethane, 4-Tert-butyl-4'-methoxydibenzoylmethane, 2-Methyl-5-isopropyl-4'-methoxydibenzoylmethane, 2-Methyl-5-tert-butyl-4'-methoxydibenzoylmethane, 2,4-Dimethyl-4'-methoxydibenzoylmethane, 2,6-Dimethyl-4-tert-butyl-4'-methoxydibenzoylmethane.

Particularly preferred is 4-(tert-butyl)-4'-methoxydibenzoylmethane also identified as 1(p-tert butylphenyl)-3-(p-methoxyphenyl)-1,3-proponedione CAS 70356-09-1 (the generic name being Avobenzone), commercially available under the trademark "Parsol 1789" by Roche or "Eusolex 9020" by Merck KGaA/EMD Chemicals. This sunscreen has the following structural formula.

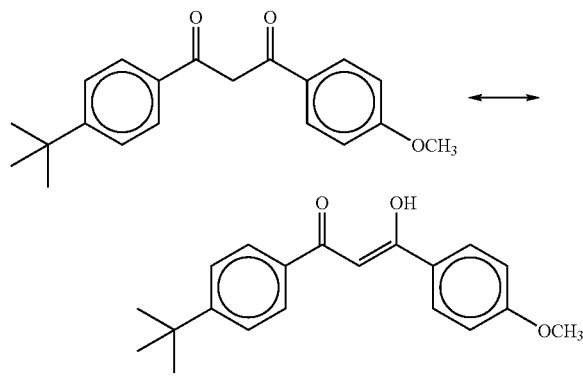

The enol-form of Avobenzone is the preferred sunscreen.

The dibenzoylmethane derivative or derivatives can be present in the preferred composition in a concentration ranging from 0.5% to 35% by weight and preferably ranging from 10% to 25% by weight with respect to the total weight of the composition.

The photostabilizer compounds of the composition are compounds with sunscreen activity, i.e. they are chromophoric within the ultra violet radiation range of from 290–400 nm and also exhibit antioxidant properties. These compounds are represented by general formula I.

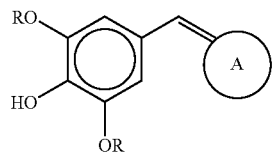

In formula I, A is a moiety which provides chromophoric properties within the UV radiation range of 290–400 nm. This moiety comprises one divalent group or two monovalent groups with at least one group having carbonyl (C=O) functionality. For formula I, each R is independently linear or branched $C_1$–$C_8$ alkyl. The one or more compounds of formula I can preferably stabilize an additional sunscreening agent against photodegradation from exposure to sunlight.

Preferred compounds are of formula II below.

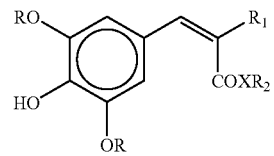

wherein, each R is independently linear or branched $C_1$ to $C_8$ alkyl;

$R_1$ is selected from the group consisting of —C(O)CH$_3$, —CO$_2$R$_3$, —C(O)NH$_2$, and C(O)N(R$_4$)$_2$ and —CN;

X is O or NH;

$R_2$ is linear or branched $C_1$ to $C_{20}$ alkyl;

$R_3$ is linear or branched $C_1$ to $C_{20}$ alkyl; and each $R_4$ is independently hydrogen or linear or branched $C_1$ to $C_8$ alkyl.

Included within the preferred compounds are those of formula II wherein R is linear or branched $C_1$–$C_4$ alkyl, X is oxygen and $R_2$ is linear or branched $C_1$–$C_{12}$ alkyl. Of these compounds, those more preferred have $R_1$ as C(O)CH$_3$ or CO$_2$R$_3$ wherein $R_3$ is a linear or branched $C_1$ to $C_4$ alkyl. For compounds wherein $R_1$ is C(O)N(R$_4$)$_2$, $R_4$ is preferably hydrogen or a linear or branched $C_1$–$C_4$ alkyl.

While compounds having from $C_1$–$C_4$ alkyl groups for $R_2$ and $R_3$ are preferred, significant utility can be obtained from compounds wherein $R_2$ and $R_3$ are linear or branched $C_8$ to $C_{20}$ alkyl or $C_{12}$ to $C_{20}$ alkyl groups.

A preferred class of compounds is that of formulae III or IV wherein $R_1$ and $R_2$ are as defined for formula I with $R_3$ is $C_1$–$C_8$ alkyl and $R_4$ is $C_1$–$C_4$ alkyl.

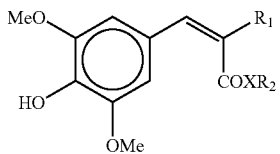

-continued

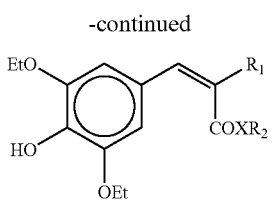

Preferred compounds include those selected from the group consisting of
ethyl-alpha-cyano-3,5-dimethoxy-4-hydroxy cinnamate,
ethyl-alpha-acetyl-3,5-dimethoxy-4-hydroxy cinnamate,
iso-propyl-alpha-acetyl-3,5-dimethoxy-4-hydroxy cinnamate,
iso-amyl-alpha-acetyl-3,5-dimethoxy-4-hydroxy cinnamate,
2-ethylhexyl-alpha-acetyl-3,5-dimethoxy-4-hydroxy cinnamate,
diethyl-3,5-dimethoxy-4-hydroxy benzylidene malonate,
di-(2-ethylhexyl)-3,5-dimethoxy-4-hydroxy benzylidene malonate,
diisoamyl-3,5-dimethoxy-4-hydroxy benzylidene malonate,
didodecyl-3,5-dimethoxy-4-hydroxy benzylidene malonate,
dipalmitoyl-3,5-dimethoxy-4-hydroxy benzylidene malonate, and
di-isopropyl-3,5-dimethoxy-4-hydroxy benzylidene malonate.

There is also provided by the present invention additional photostabilizer compounds with sunscreen and antioxidant functionality. These compounds are represented by general formula V.

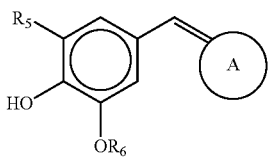

In formula V, A is a moiety which provides chromophoric properties within the UV radiation range of 290–400 nm. This moiety comprises one divalent group or two monovalent groups with at least one group having carbonyl (C=O) functionality. For formula V, each $R_6$ is independently linear or branched $C_1$–$C_8$ alkyl and $R_5$ is hydrogen or $R_6$. The one or more compounds of formula V can preferably stabilize an additional sunscreening agent against photodegradation from exposure to sunlight. Preferred compounds are of formula VI below.

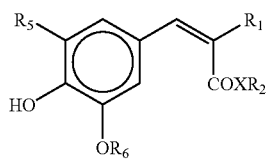

For formula VI,
$R_1$ is selected from the group consisting of —C(O)CH$_3$, —CO$_2$R$_3$, —C(O)NH$_2$, C(O)N(R$_4$)$_2$ and —CN;
X is O or NH;
$R_2$ is linear or branched $C_1$ to $C_{30}$ alkyl;
$R_3$ is linear or branched $C_1$ to $C_{20}$ alkyl;
each $R_4$ is independently hydrogen or linear or branched $C_1$ to $C_8$ alkyl;
$R_5$ is linear or branched $C_1$–$C_8$ alkyl or hydrogen; and
$R_6$ is linear or branched $C_1$–$C_8$ alkyl.

The one or more compounds of formula IV can preferably stabilize a sunscreen agent against photodegradation from sun exposure to sunlight.

Included within the preferred compounds are those of formula VI wherein $R_1$ is linear or branched $C_1$–$C_4$ alkyl, X is oxygen and $R_2$ is linear or branched $C_1$–$C_{12}$ alkyl. Of these compounds, those more preferred have $R_1$ as C(O)CH$_3$ or CO$_2$R$_3$ wherein $R_3$ is a linear or branched $C_1$ to $C_4$ alkyl. For compounds wherein $R_1$ is C(O)N(R$_4$)$_2$, $R_4$ is preferably hydrogen or a linear or branched $C_1$–$C_4$ alkyl.

While compounds having from $C_1$–$C_4$ alkyl groups for $R_2$ and $R_3$ are preferred, significant utility can be obtained from compounds wherein $R_2$ and $R_3$ are linear or branched $C_8$ to $C_{20}$ alkyl or $C_{12}$ to $C_{20}$ alkyl groups.

Another preferred class of compounds are those of formulae VII and VIII wherein $R_1$ and $R_2$ are as defined for formula IV with $R_3$ being $C_1$–$C_8$ alkyl and $R_4$ being $C_1$–$C_4$ alkyl.

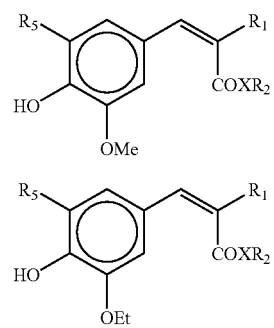

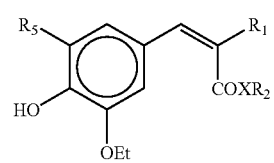

Examples of compounds consistent with Formula VII or VIII include those selected from the group consisting of
ethyl-alpha-cyano-3-methoxy-4-hydroxy cinnamate,
ethyl-alpha-acetyl-3-methoxy-4-hydroxy cinnamate,
iso-propyl-alpha-acetyl-3-methoxy-4-hydroxy cinnamate,
iso-amyl-alpha-acetyl-3-methoxy-4-hydroxy cinnamate,
2-ethylhexyl-alpha-acetyl-3-methoxy-4-hydroxy cinnamate,
diethyl-3-methoxy-4-hydroxy benzylidene malonate,
di-(2-ethylhexyl)-3-methoxy-4-hydroxy benzylidene malonate,
diisoamyl-3-methoxy-4-hydroxy benzylidene malonate,
didodecyl-3-methoxy-4-hydroxy benzylidene malonate,
dipalmitoyl-3-methoxy-4-hydroxy benzylidene malonate,
di-isopropyl-3-methoxy-4-hydroxy benzylidene malonate,
di-(2-ethyhexyl)-3-methoxy-4-hydroxy-5-isopropyl-benzylidene malonate,
di-isoamyl-3-methoxy-4-hydroxy-5-tert.butyl-benzylidene malonate,
iso-amyl-alpha-acetyl-3-methoxy-4-hydroxy-5-isopropyl cinnamate, and
iso-amyl-alpha-acetyl-3-methoxy-4-hydroxy-5-tert.butyl cinnamate.

The present invention also provides sunscreen formulations, which comprise at least one compound of formula I–VIII. Amounts of the compounds of formula I–VIII within such compositions typically range from 0.1 to 40 wt % based on the total weight of the sunscreen. These sunscreen formulations can contain one or more additional organic sunscreen agents for filtering UV-B and/or UV-A rays or they may additionally contain one or more metal oxide sunscreen agents such as titanium dioxide or zinc oxide.

These sunscreen formulations may additionally contain a carrier and at least one component selected from the group consisting of dispersing agents, preservatives, anti-foams, perfumes, oils, waxes, propellants, dyes, pigment emulsifiers, surfactants, thickeners, humectants, exfoliants and emollients. These sunscreen formulations may be in the form of a cosmetic composition with a cosmetically acceptable carrier and one or more cosmetic adjuvants. The sunscreen formulation can optionally have conventional antioxidants or other stabilizers, which do not have UV absorbing characteristics.

Methods of using these sunscreen compositions and methods for improving the photostability of sunscreen formulations are also provided. The methods of using the sunscreen formulations comprise applying a sunscreen formulation which contains a compound of formula I–VIII to a substrate. Preferred substrates are skin and hair. To improve the photostability of a sunscreen formulation, a compound of formula I–VIII is added to the sunscreen formulation in an amount sufficient to reduce the loss of UV absorbance of the sunscreen as it is irradiated. Typical amounts fall within the range of 0.1% to 40 wt %, based on the total weight of said sunscreen formulation. More typically, the amount falls within the range of 1 wt % to 25 wt %. The amount of organic sunscreen compound of formulae I–VIII, preferably ranges from about 3 wt % to about 15 wt % of the sunscreen formulation. Other ingredients referred to above and discussed more particularly below are generally used in an amount from about 0.1 wt % to about 10 wt % of the sunscreen formulation. The balance comprises a cosmetically or pharmaceutically acceptable carrier.

The sunscreen formulations may contain dispersing agents, emulsifiers or thickening agents to assist in applying a uniform layer of the active compounds. Suitable dispersing agents for the sunscreen formulations include those useful for dispersing organic or inorganic sunscreen agents in either a water phase, an oil phase, or part of an emulsion, including, for example, chitosan.

Emulsifiers may be used in the sunscreen formulations to disperse one or more of the compounds of formulae I–VIII or other component of the sunscreen formulation. Suitable emulsifiers include conventional agents such as, for example, glycerol stearate, stearyl alcohol, cetyl alcohol, dimethicone copolyol phosphate, hexadecyl-D-glucoside, octadecyl-D-glucoside, etc.

Thickening agents may be used to increase the viscosity of the sunscreen formulations. Suitable thickening agents include carbomers, acrylate/acrylonitrile copolymers, xanthan gum and combinations of these. The carbomer thickeners include the crosslinked CARBOPOL acrylic polymers from B. F. Goodrich. The amount of thickener within the sunscreen formulation, on a solids basis without water, may range from about 0.001 to about 5%, preferably from 0.01 to about 1% and optimally from about 0.1 to about 0.5% by weight.

Minor optional adjunct ingredients for the sunscreen formulations to be applied to skin or hair may include preservatives, waterproofing agents, fragrances, anti-foam agents, plant extracts (Aloe vera, witch hazel, cucumber, etc) opacifiers, skin conditioning agents and colorants, each in amounts effective to accomplish their respective functions.

The sunscreen formulations may optionally contain an ingredient which enhances the waterproof properties such as, compounds that form a polymeric film, such as dimethicone copolyol phosphate, diisostearoyl trimethyolpropane siloxysilicate, chitosan, dimethicone, polyethylene, polyvinylpyrrolidone/vinylacetate, PVP/Eiconsene copolymer and adipic acids/diethylene glycol/glycerine crosspolymer etc. Waterproofing agents may be present at levels of from about 0.01 to about 10% by weight.

The sunscreen formulations may also optionally contain one or more skin conditioning agents. These include humectants, exfoliants and emollients.

Humectants are polyhydric alcohols intended for moisturizing, reducing scaling and stimulating the removal of built scale from the skin. Typically polyhydric alcohols include polyalkylene glycols and more preferably alkylene polyols and their derivatives. Illustrative are propylene glycol, dipropylene glycol, polypropylene glycol, polyethylene glycol, sorbitol, 2-pyrrolidone-5-carboxylate, hydroxypropyl sorbitol, hexylene glycol, ethoxydiglycol 1,3-butylene glycol, 1,2,6-hexanetriol, glycerin, ethoxylated glycerin, propoxylated glycerin and mixtures thereof. Most preferably the humectant is glycerin. Amounts of humectant can range anywhere from 1 to 30%, preferably from 2 to 20% and optimally from about 5 to 10% by weight of the sunscreen composition.

The exfoliants suitable for use in the present may be selected from alpha-hydroxy carboxylic acids, beta hydroxycarboxylic acids and salts of these acids. Most preferred are glycolic, lactic and salicylic acids and their alkali, metal or ammonium salts.

Suitable emollients include those agents known for softening the skin or hair, which may be selected from hydrocarbons, fatty acids, fatty alcohols and esters. Petrolatum is a common hydrocarbon type of emollient conditioning agent. Other hydrocarbons that may be employed include alkyl benzoate, mineral oil, polyolefins such as polydecene, and paraffins, such as isohexadecane. Fatty acids and alcohols typically have from about 10 to 30 carbon atoms. Illustrative are myristic, isostearic, hydroxystearic, oleic, linoleic, ricinoleic, behenic and eruicic acids and alcohols. Ester emollients may be those selected from one or more of the following, triglyceride esters, acetoglyceride esters, ethoxylated glycerides, alkyl esters of fatty acids, ether esters, polyhydric alcohol esters and wax esters. Additional emollients or hydrophobic agents include $C_{12}$ to $C_{15}$ alkyl benzoate, dioctyladipate, octyl stearate, octyldodecanol, hexyl laurate, octyldodecyl neopentanoate, cyclomethicone, dicapryl ether, dimethicone, phenyl trimethicone, isopropyl myristate, capriylic/capric glycerides, propylene glycol dicaprylate/dicaprate and decyl oleate.

The sunscreen formulations may optionally contain one or more long chain fatty alcohols or esters or amides or combination thereof, preferably liquid in nature and able to solubilize the dibenzoylmethane derivative preferably to at least 15%. These alcohols or esters can be used alone or in combination as a co-solubilizer with organic UV-B sunscreens. Exemplary long chain alcohols or esters according to the present invention include: cocoglycerides, decyloleate, C-12-15 alkyl benzoate, caprylic/capric triglycerides, cetaryl ethylhexylhexanoate, dioctyl adipate, glyceryl dilaurate, stearamide, dimethylbehanamide, b-alanin derivatives, such as, ethyl butylacetylamino propoane (IR 3535) etc. A long chain fatty alcohol or ester is typically present in an amount ranging from 0 to 80%.

The sunscreen formulations may optionally contain one or more inorganic sunscreen agents as discussed above including micro fine surface treated titanium dioxide and micro fine untreated and surface treated zinc oxide. Titanium dioxide in the sunscreen compositions preferably has a mean primary particle size of between 5 and 150 nm and preferably from 10 to 100 nm. Titanium oxide may have anatase, rutile or amorphous structure. The zinc oxide in the sunscreen compositions preferably has a mean primary particle size of between 5 nm and 150 nm, preferably between 10 nm and 100 nm. Examples of modified titanium dioxide compositions include:

Eusolex® T-45D (surface treated with alumina and simethicone, 45% dispersion in isononoyl isononoate);

Eusolex® T-Aqua, (surface treated with aluminum hydroxide, 25% dispersion in water); and Eusolex® T-2000 (surface treated with alumina and simethicone), all available from MERCK KGaA/EMD Chemicals.

The sunscreen formulation may also contain one or more additional monomeric organic chromophoric compounds. These can either be UV-A, UV-B or broad band filters, Examples of suitable UV-A sunscreens include benzophenone derivatives, menthyl anthranilate, butyl methoxydibenzoyl methane, and benzylidene-dioxoimidazoline derivatives.

UV-B organic sunscreens are preferably liquid in nature and preferably can solubilize the dibenzoylmethane derivative preferably to at least 15%. Examples of suitable UV-B sunscreens include cinnamate, salicylate and diphenylacrylate, derivatives thereof and combinations thereof. Preferred UV-B sunscreens are salicylates or cinnamtes alone or in combination. Particularly, preferred UV-B organic sunscreens according to the present invention include salicylate derivatives and cinnamate derivatives.

Salicylates, such as homosalate, ethylhexyl salicylate and dipropylene glycol salicylate, are UV-B absorbers having a $\lambda_{max}$~306 nm.

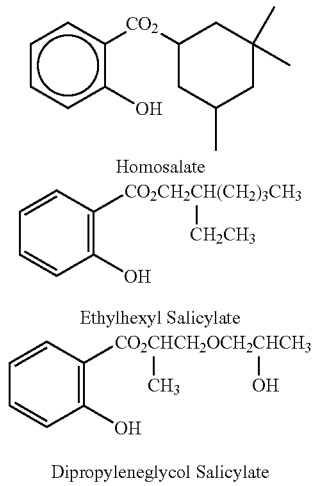

Other salicylates are also encompassed by the present invention. A composition of the invention optionally contains at least one salicylate present in an amount ranging from 0 to 80%.

Cinnamate derivatives, such as ethylhexyl methoxycinnamate (4A), isoamyl-p-methoxycinnamate (4B), cinoxate (4C), isopropyl methoxycinnamate (4D), diisopropyl methyl cinnamate (4E)) and glyceryl ethylhexanoate dimethoxycinnamate (4F), are all UV-B absorbers having a $\lambda_{max}$~310 nm.

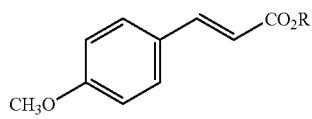

4A: Ethylhexyl Methoxycinnamate: R=2-Ethyhexl
4B: Isoamyl Methoxycinnamate: R=Isoamyl
4C: Cinnoxate: R=2-Ethoxyethyl
4D: Isopropyl Methoxycinnamate: R=Isopropyl

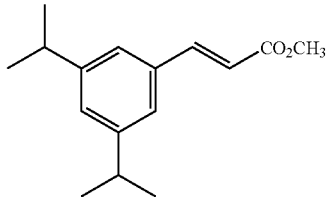

4E: Diisopropyl Methyl Cinnamate

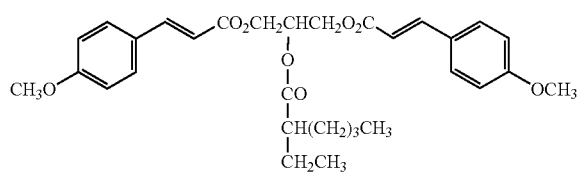

4F: Glyceryl ethylhexanoate Dimethoxycinnamate

Other cinnamates are also encompassed by the present invention. A composition of the invention optionally contains at least one cinnamate present in an amount ranging from 0 to 80%.

Examples of suitable broad-band sunscreen include benzotriazole derivatives and triazine derivatives such as anisotriazone. Others include ethylhexyltriazone and diethylhexylbutamidotriazone.

Particularly useful organic sunscreen agents that can be introduced are 2-ethylhexyl p-methoxycinnamate, 4,4'-t-butylmethoxydibenzoyl methane, 2 hydroxy-4-methoxybenzophenone, octyldimethyl p-aminobenzoic acid, 2,2-dihydroxy-4-methoxybenzophenone, ethyl-4-[bis(hydroxypropyl)]aminobenzoate, 2-ethylhexyl-2-cyano-3,3-diphenylacrylate, 2-ethylhexylsalicylate, glycerol p-aminobenzoate, 3,3,5-trimethylcyclohexylsalicylate, methylanthranilate, p-dimethylaminobenzoic acid, 2-ethyl hexyl p-dimethylaminobenzoate, 2-phenylbenzimidazole-5-5-sulfonic acid, 2-(p-dimethylamino phenyl-5-sulfoniobenzoxazoic acid and mixtures thereof.

Examples of useful commercially available organic sunscreen agents that can be introduced include 2-phenylbenzimidazole-5-sulphonic acid, 2-(4-methylbenzylidene)-camphor, 4-isopropyldibenzoyl methane all of the Eusolex™ series sold by EMD Chemicals, Inc., USA and Merck KGaA, Darmstadt, Germany.

The sunscreen formulation may contain an additional antioxidant. Examples of suitable antioxidants which provide stability include p-hydroxybenzoic acid and its derivatives (ethylisobutyl, glyceryl esters of p-hydroxybenzoic acid); salicylates (octylamyl, phenyl, benzyl menthyl, glycerol and dipropyleneglycol esters); cumarin derivatives; flavones; hydroxy or methoxy substituted benzophenones; uric or tannic acid and its derivatives.

In addition to providing sunscreen activity at levels, which provide U. V. absorption, the compounds of Formula I to VIII can be introduced into a skin care formulation, a hair care formulation or other personal care formulations such as cosmetic formulations at levels which provide antioxidant activity. These compounds can be used with or without conventional antioxidants in personal care formulations such as hair care, skin care and cosmetic formulations.

The personal care formulations can be in the form of creams, ointments, suspensions, powders, oil, lotions, oleo alcoholic lotions, fatty gels, oleo-alcoholic gels and lotions, solid sticks, foams, emulsions, liquid dispersions, sprays and aerosols. More specific cosmetic forms include: lipsticks, foundations, makeup, loose or press powder, eye blush, eye shadow and nail lacquer.

The sunscreen formulations of this invention preferably offer protection from UV radiation with wavelengths of about 290 nm to 400 nm and preferably from wavelengths in the range of about 290–370 nm. Sunscreen formulations of this invention also typically have a sunscreening protection factor (SPF) range of from about 2 to 60, with a preferred SPF range of from about 10 to about 45. The target SPF range can be achieved with a combination of both inorganic and organic chromophoric compounds. SPF is determined by techniques well known in the art, on human skin as described in the Federal Register, Aug. 25, 1978, Vol. 43, No. 166, pages 38259–38269 (Sunscreen Drug Products for Over-The-Counter Human Use, Food and Drug Administration). SPF values can also be approximated using in-vitro models as described, for example, in J. Soc. Cosmet. Chem. 44:127–133 (May/June 1989).

Sunscreen formulations of this invention can be prepared as described by conventional means.

EXAMPLE I

Sunscreen Lotions with Avobenzone (2% Avobenzone+2% Photostabilizer)

| INCI Name | Trade Name/Supplier | % W/W |
|---|---|---|
| Phase A-1 | | |
| Deionized water | | Qs 100 |
| Disodium EDTA | | 0.05 |
| Butylene Glycol | | 3.00 |
| Methylparaben | | 0.15 |
| Phase A-2 | | |
| Carbomer | Carbopol Ultrez 10/Goodrich | 0.20 |
| Phase B | | |
| Isopropyl myristate | Emerest 2314/Cognis | 2.50 |
| Cetyl alcohol, gylceryl stearate, PEG-75, ceteth-20, and steareth-20 | Emolium Delta/Gattefosse | 4.00 |
| Dimethicone | DC 200 fluid, 100 ct | 1.00 |
| C30–38 Olefin/Isopropyl Maleate/MA copolymer | Performa V 1608/New Phase Technologies | 1.00 |
| C12–15 Alkyl benzoate | Finsolv TN/Finetex | 12.00 |
| Butyl methoxydibenzoylmethane | Eusolex 9020/Rona | 2.00 |
| Photostabilizer* | | 2.0–6.0 |
| Phase C | | |
| Triethanolamine (99%) | TEA 99%/Union Carbide | 0.30 |
| Phase D | | |
| Phenoxyethanol (and) Isopropylparaben (and) isobutylparaben (and) Butyl-parben | Liquapar PE/ISP | 1.00 |

*Photostabilizers used were Di-2-ethylhexyl-3,5-dimethoxy-4-hydroxy-benzylidene malonate (PR/SCP-2/40) or Corapan TQ (Diethylhexy-2,6-napthalate, H&R)

Procedure:

Disperse Phase A-2 in Phase A-1 under agitation. Heat to 70–75° C. Combine Phase B ingredients. Stir and heat to 70–75°. Add Phase B to Phase A while stirring. Add Phase C. Homogenize until mixture cools to 40–45° C. Add Phase D. Stir allowing mixture to cool to RT.

EXAMPLE 2

Sunscreen Lotions with Avobenzone (2% Avobenzone+6% HMS+2% Photostabilizer)

| INCI Name | Trade Name/Supplier | % W/W |
|---|---|---|
| Phase A-1 | | |
| Deionized water | | Qs 100 |
| Disodium EDTA | | 0.05 |
| Butylene Glycol | | 3.00 |
| Methylparaben | | 0.15 |
| Phase A-2 | | |
| Carbomer | Carbopol Ultrez 10/Goodrich | 0.20 |
| Phase B | | |
| Cocoglyceride | Myritol 331/Cognis | 4.00 |
| Cetyl alcohol, gylceryl stearate, PEG-75, ceteth-20, and steareth-20 | Emolium Delta/Gattefosse | 4.00 |
| Dimethicone | DC 200 fluid, 100 ct | 1.00 |
| C30–38 Olefin/Isopropyl Maleate/MA copolymer | Performa V1608/New Phase Technologies | 1.00 |
| C12–15 Alkyl benzoate | Finsolv TN/Finetex | 12.00 |
| Homosalate | Eusolex HMS/Rona | 6.00 |
| Butyl methoxydibenzoylmethane | Eusolex 9020/Rona | 2.00 |
| Photostabilizer* | | 2.0 |
| Phase C | | |
| Triethanolamine (99%) | TEA 99%/Union Carbide | 0.30 |
| Phase D | | |
| Phenoxyethanol (and) Isopropylparaben (and) isobutylparaben (and) Butyl-parben | Liquapar PE/ISP | 1.00 |

*Photostabilizers used were Di-2-ethylhexyl-3,5-dimethoxy-4-hydroxy-benzylidene malonate (PR/SCP-2/40) or Corapan TQ (Diethylhexy-2,6-napthalate, H&R)

Procedure:

Disperse Phase A-2 in Phase A-1 under agitation. Heat to 70–75° C. Combine Phase B ingredients. Stir and heat to 70–75°. Add Phase B to Phase A while stirring. Add Phase C. Homogenize until mixture cools to 40–45° C. Add Phase D. Stir allowing mixture to cool to RT.

EXAMPLE 3

Sunscreen Lotion with 2% Avobenzone, 5% Octyl Methoxycinnamte & 0–6% Photostabilizer

| INCI NAME | TRADE NAME/MANUFACTURER | % w/w |
|---|---|---|
| Phase A-1 | | |
| Water (demineralized) | q.s. | 100.00 |
| Disodium EDTA | | 0.05 |
| Butylene glycol | | 3.00 |
| Methylparaben | | 0.15 |
| Phase A-2 | | |
| Carbomer | Carbopol Ultrez 10/Noveon | 0.20 |
| Phase B | | |
| Isopropyl myristate | Emerest 2314/Cognis | 2.50 |
| Cetyl alcohol, glyceryl stearate, PEG-75, ceteth-20 and steareth-20 | Emolium Delta/Gattefosse | 4.00 |
| Dimethicone | DC200 fluid, 100 cst/Dow Corning | 1.00 |
| C30–38 olefin/isopropyl maleate/MA copolymer | Performa V1608/New Phase Technologies | 1.00 |
| C12–15 alkyl benzoate | Finsolv TN/Finetex | 12.00 |
| Butyl methoxydibenzoylmethane | Eusolex 9020/Rona | 2.00 |
| Octinoxate | Eusolex 2292/Rona | 5.00 |
| Photostabilizer* | | 0, 2, 4 & 6 |
| Phase C | | |
| Triethanolamine (99%) | | 0.30 |
| Phase D | | |
| Phenoxyethanol, Isopropyl-paraben, Isobutylparaben, Butylparaben | Liquapar PE/Sutton | 1.00 |
| Total | | 100.00 |

*Photostabilizers used were Oxynex ST (proposed INCI Name: Diethylhexyl syringal malonate)/Rona and Corapan TQ (Diethylhexyl 2, 6-naphtalate,)/H&R Procedure Disperse A-2 in A-1 under agitation. Heat A to 70–75° C. Combine B and heat to 70–75° C. Add B to A while stirring. Add C. Homogenize until mixture cools to 60° C. Add phase D. Stir allowing mixture to cool to RT.

EXAMPLE 4

Sunscreen Lotion with Sol-Gel Capsule of Avobenzone, Octylmethoxy Cinnamate & Photostabilizer

| INCI NAME | TRADE NAME/MANUFACTURER | % w/w |
|---|---|---|
| Phase A-1 | | |
| Water (demineralized) | q.s. | 100.00 |
| Disodium EDTA | | 0.05 |
| Butylene glycol | | 3.00 |
| Methylparaben | | 0.15 |
| Phase A-2 | | |
| Carbomer | Carbopol Ultrez 10/Noveon | 0.20 |
| Phase B | | |
| Isopropyl myristate | Emerest 2314/Cognis | 2.50 |
| Cetyl alcohol, glyceryl stearate, PEG-75, ceteth-20 and steareth-20 | Emolium Delta/Gattefosse | 4.00 |
| Dimethicone | DC200 fluid, 100 cst/Dow Corning | 1.00 |
| C30–38 olefin/isopropyl maleate/MA copolymer | Performa V1608/New Phase Technologies | 1.00 |
| C12–15 alkyl benzoate | Finsolv TN/Finetex | 12.00 |
| Sol-gel capsule containing Butyl methoxydibenzoylmethane, Octylmethoxy cinnamte, and Photostabilizer* | Present Invention | 20.00 |
| Phase C | | |
| Triethanolamine (99%) | | 0.30 |
| Phase D | | |
| Phenoxyethanol, Isopropyl-paraben, Isobutylparaben, Butylparaben | Liquapar PE/Sutton | 1.00 |
| Total | | 100.00 |

*40% Dispersion in water containing about 20% Avobenzone, 20% Photostabilizer (Diethylhexyl 3,5-Diinethoxy-4-hydroxybenzylidene malonate) and 60% Octinoxate Procedure Disperse A-2 in A-1 under agitation. Heat A to 70–75° C. Combine B and heat to 70–75° C. Add B to A while stirring. Add C. Homogenize until mixture cools to 60° C. Add phase D. Stir allowing mixture to cool to RT.

EXAMPLE 5

Sunscreen Lotion with sol-gel capsule of Avobenzone, Hmosalate & photostabilizer Procedure is similar as described in Example 4, except Octinoxate is replaced with Homosalate.

EXAMPLE 6

Sprayable Sunscreen Lotion with Sol-Gel Capsule of Avobenzone, Solubilizer & Photostabilizer

| INCI NAME | TRADE NAME/MANUFACTURER | % w/w |
|---|---|---|
| Phase A | | |
| PEG-30 Dipolyhydroxystearate | Arlacel P135/Uniqema | 3.00 |
| Hexyl Laurate | Cetiol A/Cognis | 5.50 |
| Isohexadecane | Arlamol HD | 8.00 |
| Caprylic/Capric Triglyceride | Miglyol 812 N | 4.00 |
| Diocyl Adipate | Crodamol DOA | 4.00 |
| Phase B | | |
| Magnesium Sulfate | Magnesium Sulfate/Merck KGaA | 0.70 |

-continued

| INCI NAME | TRADE NAME/MANUFACTURER | % w/w |
| --- | --- | --- |
| Glycerine | Glycerol (about 87%)//Merck KGaA | 3.00 |
| Disodium EDTA | Titriplex III Merck KGaA | 0.05 |
| Water | | 46.05 |
| Phase C | | |
| Present Invention | Sol-gel capsule containing Butyl methoxydibenzoyl-methane, cocoglyceride, and Photostabilizer* | 20.00 |
| Phase D | | |
| Titanium Dioxide, Alumina, Stearic acid | Eusolex TS/Merck KGaA | 5.00 |
| Phase E | | |
| Phenoxyethanol, Isopropyl-paraben, Isobutylparaben, Butylparaben | Liquapar PE/Sutton | 0.70 |
| Total | | 100.00 |

*40% Dispersion in water containing about 20% Avobenzone, 20% Photostabilizer (Diethylhexyl 3,5-Dimethoxy-4-hydroxybenzylidene malonate) and 60% cocoglyceride Procedure Combine phases A and B and heat to 80 C. Add phase B slowly to phase A while stirring vogorously. Homogenize. Allow to cool down while stirring and add phase C at 40 C, disperse Eusolex TS and finally add phase E. Stir to cool.

It has been found that to provide antioxidant functionality, the phenyl group of the compounds of formula I should have a substituent pattern of "3,5-alkoxy, 4-hydroxy." Compounds of formula I also have an extended conjugation with aromatic ring providing UV absorbing functionality, (chromophoric in the UV range). Non-aromatic functionality can vary widely in structure with examples given in formulae II, III, and IV above.

The compounds of Formula I–IV can be obtained by condensation of a corresponding 3,5-dialkoxy, 4-hydroxy benzaldehyde of formula B,

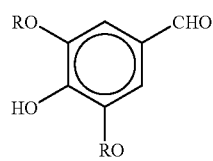

B wherein R is as defined above, with a compound that provides the UV absorbing moiety, "A" as defined above. An example is a compound of the formula: $R_1$—$CH_2$—$C(O)XR_2$ wherein $R_1$ and $R_2$ and X are as defined above for formulae II–IV.

The benzaldehyde of formula B can be obtained commercially or prepared from 3, 4, 5-trimethoxybenzaldehyde through selective monodemethylation at the 4-position. Alternately, syringaldehyde can be prepared from 3-methoxy-4-hydroxy-5-bromo benzaldehyde by replacing bromine with methoxy using sodium methoxide. This technique leads to syringaldehyde. The syringaldehyde is then condensed with a malonate ester or acetyl acetoacetate or similar compounds to provide the desired UV absorbing structure.

Methods of preparation of two compounds of the invention are illustrated below.

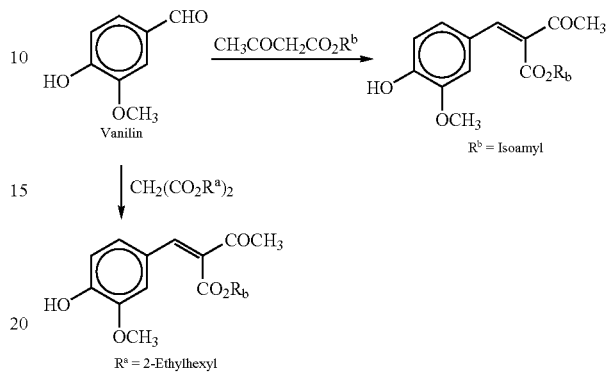

In one embodiment, the invention relates to a sunscreen composition comprising i) at least one UV-A organic sunscreen and ii) at least one compound of formula II

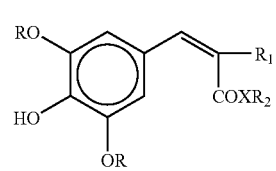

II wherein each R is independently linear or branched $C_1$ to $C_8$ alkyl; $R_1$ is selected from the group consisting of —C(O)CH$_3$, —CO$_2$R$_3$, —C(O)NH$_2$, —C(O)N(R$_4$)$_2$ and —CN; X is O or NH; $R_2$ is linear or branched $C_1$ to $C_{20}$ alkyl; $R_3$ is linear or branched $C_1$ to $C_{20}$ alkyl; and each $R_4$ is independently hydrogen or linear or branched $C_1$ to $C_8$ alkyl and said composition optionally contains at least one UV-B liquid organic sunscreen and/or at least one solubilizer.

In another embodiment the sunscreen composition of the invention is prepared by sol gel encapsulation.

In another embodiment, $R_1$ in Formula II is selected from the group consisting —C(O)CH$_3$, —CO$_2$R$_3$, —C(O)NH$_2$ and —C(O)N(R$_4$)$_2$. In another embodiment, R is $C_1$–$C_4$ alkyl, X is oxygen and $R_2$ is linear or branched $C_1$ to $C_4$ alkyl. In yet another embodiment, $R_1$ is CO$_2$R$_3$ and $R_3$ is linear or branched $C_1$ to $C_4$ alkyl. In another embodiment, $R_1$ is C(O)CH$_3$. In yet another embodiment $R_1$ is —C(O)N(R$_4$)$_2$, and at least one $R_4$ is hydrogen and the other is hydrogen or linear or branched $C_1$ to $C_4$ alkyl. In another embodiment, $R_1$ is —C(O)N(R$_4$)$_2$, and each $R_4$ is independently linear or branched $C_1$ to $C_4$ alkyl. In yet another embodiment, R is $C_1$–$C_4$ alkyl, $R_1$ is —CO$_2$R$_3$, and at least one of $R_2$ and $R_3$ is linear or branched $C_8$ to $C_{20}$ alkyl. In another embodiment, $R_2$ and $R_3$ are each linear or branched C8 alkyl. In yet another embodiment, at least one of $R_2$ and $R_3$ is linear or branched $C_{12}$ to $C_{20}$ alkyl. In another embodiment, R is methyl or ethyl.

In another embodiment, the UV-A organic sunscreen is 4-(tert-butyl)-4'-methoxydibenzoylmethane and said compound of formula II is di-2-ethylhexyl-3,5-dimethoxy-4-hydroxy-benzalmalonate. In another embodiment, the 4-(tert-butyl)-4'-methoxydibenzoylmethane and di-2-ethylhexyl-3,5-dimethoxy-4-hydroxy-benzalmalonate are in a ratio of 1:2 or 1:3. In yet another embodiment, the UV-A organic sunscreen is 4-(tert-butyl)-4'-methoxydibenzoylmethane and said compound of formula II is di-2-ethylhexyl-3,5-dimethoxy-4-hydroxy-benzalmalonate and Homosalate.

In another embodiment, the UV-A organic sunscreen is 4-(tert-butyl)-4'-methoxydibenzoylmethane and said compound of formula II is di-2-ethylhexyl-3,5-dimethoxy-4-hydroxy-benzalmalonate. In another embodiment, the 4-(tert-butyl)-4'-methoxydibenzoylmethane and di-2-ethylhexyl-3,5-dimethoxy-4-hydroxy-benzalmalonate are in a ratio of 1:2 or 1:3. In yet another embodiment, the UV-A organic sunscreen is 4-(tert-butyl)-4'-methoxydibenzoylmethane and said compound of formula II is di-2-ethylhexyl-3,5-dimethoxy-4-hydroxy-benzalmalonate and Octyl methoxy cinnamate (Octinoxate).

In another embodiment, the sunscreen composition comprises i) at least one UV-A organic sunscreen and ii) at least one compound of formula III or IV

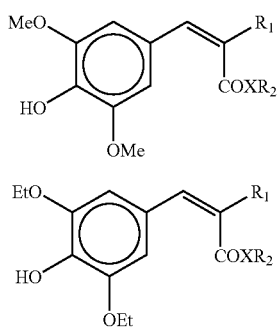

wherein $R_1$ is selected from the group consisting —C(O)CH$_3$, —CO$_2$ (C$_1$–C$_8$ alkyl), —C(O)NH$_2$, —C(O)N(C$_1$–C$_4$ alkyl)$_2$ and —CN; X is O or NH; and $R_2$ is C$_1$–C$_{12}$ alkyl and said composition optionally contains at least one UV-B liquid organic sunscreen and/or at least one solubilizer.

In another embodiment the sunscreen composition of the invention is prepared by sol gel encapsulation.

In another embodiment, $R_1$ of formula III or IV is selected from the group consisting —C(O)CH$_3$, —CO$_2$ (C$_1$–C$_8$ alkyl), —C(O)NH$_2$, —C(O)NH(C$_1$–C$_4$ alkyl), and —C(O)N(C$_1$–C$_4$ alkyl)$_2$. In another embodiment, X is oxygen and $R_2$ is linear or branched C$_1$ to C$_4$ alkyl and $R_1$ is selected from the group consisting of —CO$_2$(C$_1$–C$_4$ alkyl); —C(O)NH(C$_1$–C$_4$ alkyl), —C(O)CH$_3$, —C(O)NH$_2$, and —C(O)N (C$_1$–C$_4$ alkyl)$_2$. In yet another embodiment, $R_1$ is —CO$_2$C$_8$H$_{18}$.

In another embodiment, the compound of formula II is selected from the group consisting of ethyl-alpha-acetyl-3,5-dimethoxy-4-hydroxy cinnamate; iso-propyl-alpha-acetyl-3,5-dimethoxy-4-hydroxy cinnamate; iso-amyl-alpha-acetyl-3,5-dimethoxy-4-hydroxy cinnamate; 2-ethylhexyl-alpha-acetyl-3,5-dimethoxy-4-hydroxy cinnamate; diethyl-3,5-dimethoxy-4-hydroxy benzylidene malonate; di-(2-ethylhexyl)-3,5-dimethoxy-4-hydroxy benzylidene malonate; diisoamyl-3,5-dimethoxy-4-hydroxy benzylidene malonate; dipalmitoyl-3,5-dimethoxy-4-hydroxy benzylidene malonate; di-dodecyl-3,5-dimethoxy-4-hydroxy benzylidene malonate; and di-isopropyl-3,5-dimethoxy-4-hydroxy benzylidene malonate.

In another embodiment, the compound of formula II is present in an amount effective to adsorb illumination in a range from 290 to 400, preferably above 320 nm wavelength.

In one embodiment, the sunscreen composition comprises from 0.1 to 40 wt. % of a compound of formula II, and optionally contains an additional organic sunscreen agent for filtering UV-B rays, UV-A rays or both, said agent may be an inorganic metal oxide sunscreen agent. Preferably, the compound of Formula II stabilizes the additional sunscreen agent against degradation from exposure to light.

In another embodiment, the invention relates to a personal care composition that comprises i) at least one UV-A organic sunscreen; ii) at least one compound of formula If

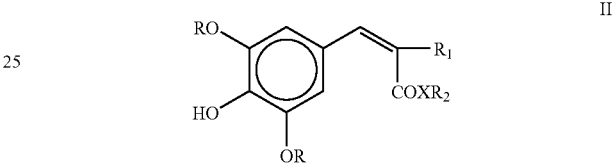

wherein each R is independently linear or branched C$_1$ to C$_8$ alkyl; $R_1$ is selected from the group consisting —C(O)CH$_3$, —CO$_2$R$_3$, —C(O)NH$_2$ and —C(O)N(R$_4$)$_2$; X is O or NH; $R_2$ is linear or branched C$_1$ to C$_{20}$ alkyl; $R_3$ is linear or branched C$_1$ to C$_{20}$ alkyl; and each $R_4$ is independently hydrogen or linear or branched C$_1$ to C$_8$ alkyl; iii) at least one UV-B liquid organic sunscreen; iv) at least one solubilizer, v) a cosmetically acceptable carrier; and vi) at least one cosmetic adjuvant selected from the group consisting of preservatives, antifoams, perfumes, oils, waxes, propellants, dyes, pigments, waterproofing agents, emulsifiers, surfactants, thickeners, humectants, exfoliants and emollients, wherein said a compound of formula II is present in an amount effective to absorb illumination in a range above 320 nm wavelength.

In another embodiment, the personal care composition is in a form selected from the group consisting of creams, ointment, suspensions, powders, oily lotions, oleo-alcoholic lotions, fatty gels, oleo-alcoholic gels, solid sticks, foams, emulsions, liquid dispersions, sprays and aerosols, preferably lipsticks, foundation, make-up, loose or press powder, eye blush, eye shadows or nail lacquer.

In yet another embodiment, the personal care composition further comprises an antioxidant other than a compound of formula II. The antioxidant may be, for example, a Tocopherol, tocopherylacetate, Ascorbic acid, Emblica antioxidants, Proanthocyanidins, Rosemary antioxidants, green tea polyphenols, gallic acid, ellagic acid, butylhydroxy toluene (BHT) and butylhydroxy anisole (BHA). Preferably, the compound of formula II is present in an amount effective to protect composition ingredients from oxidation.

In another embodiment, the present invention relates to a method of protecting a substrate from UV radiation comprising applying a sunscreen composition or personal care composition of the invention to said substrate, e.g., skin or hair.

In another embodiment, the present invention relates to a sunscreen composition comprising i) at least one UV-A organic sunscreen and ii) at least one compound selected from the group consisting of ethyl-alpha-acetyl-3,5-dimethoxy-4-hydroxy cinnamate; iso-propyl-alpha-acetyl-3,5-dimethoxy-4-hydroxy cinnamate; iso-amyl-alpha-acetyl-3,5-dimethoxy-4-hydroxy cinnamate; 2-ethylhexyl-alpha-acetyl-3,5-dimethoxy-4-hydroxy cinnamate; diethyl-3,5-dimethoxy-4-hydroxy benzylidene malonate; di-(2-ethylhexyl)-3,5-dimethoxy-4-hydroxy benzylidene malonate; diisoamyl-3,5-dimethoxy-4-hydroxy benzylidene malonate; dipalmitoyl-3,5-dimethoxy-4-hydroxy benzylidene malonate; di-dodecyl-3,5-dimethoxy-4-hydroxy benzylidene malonate; and di-isopropyl-3,5-dimethoxy-4-hydroxy benzylidene malonate. The sunscreen may further comprise at least one UV-B liquid organic sunscreen and/or at least one solubilizer, and is preferably prepared by sol gel encapsulation.

In another embodiment, the sunscreen composition further comprising an antioxidant other than a compound of formula II. The antioxidant may be, for example, a Tocopherol, tocopherylacetate, Ascorbic acid, Emblica antioxidants, Proanthocyanidins, Rosemary antioxidants, green tea polyphenols, gallic acid, ellagic acid, butylhydroxy toluene (BHT) and butylhydroxy anisole (BHA).

In another embodiment, the present invention relates to a sunscreen composition comprising i) at least one UV-A organic sunscreen and ii) at least one compound of formula V

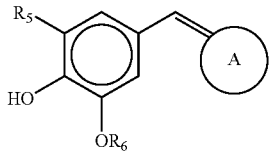

V wherein A is a moiety which is chromophoric within the UV radiation range of wavelengths to provide UV absorbing activity to the compound of formula I, wherein moiety A comprises one divalent group or two monovalent groups, with at least one group having carbonyl (C=O) functionality, $R_6$ is independently linear or branched $C_1$–$C_8$ alkyl, and $R_5$ is hydrogen or linear or branched $C_1$–$C_8$ alkyl and said composition optionally contains at least one UV-B liquid organic sunscreen and/or at least one solubilizer.

In another embodiment the sunscreen composition of the invention is prepared by sol gel encapsulation.

In another embodiment the present invention relates to a sunscreen composition comprising i) at least one UV-A organic sunscreen and ii) at least one compound of formula VI

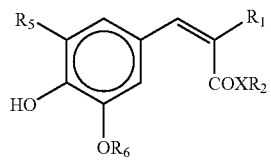

VI wherein $R_1$ is selected from the group consisting of —C(O)CH$_3$, —CO$_2$R$_3$, —C(O)NH$_2$, —C(O)N(R$_4$)$_2$, and —CN; X is O or NH; $R_2$ is linear or branched $C_1$ to $C_{30}$ alkyl; $R_3$ is linear or branched $C_1$ to $C_{20}$ alkyl; and each $R_4$ is independently hydrogen, or linear or branched $C_1$ to $C_8$ alkyl; $R_5$ is linear or branched $C_1$–$C_8$ alkyl or hydrogen, and $R_6$ is $C_1$ to $C_8$ alkyl and said composition optionally contains at least one UV-B liquid organic sunscreen and/or at least one solubilizer.

In another embodiment the sunscreen composition of the invention is prepared by sol gel encapsulation.

In yet another embodiment, $R_6$ of formula VI is $C_1$–$C_8$ alkyl, X is oxygen and $R_2$ is linear or branched $C_1$ to $C_4$ alkyl. In another embodiment, $R_1$ is CO$_2$R$_3$ and, $R_3$ is linear or branched $C_1$ to $C_8$ alkyl. In another embodiment, $R_1$ is C(O)CH$_3$. In yet another embodiment, $R_1$ is —C(O)N(R$_4$)$_2$, and at least one $R_4$ is hydrogen and the other is hydrogen or linear or branched $C_1$ to $C_4$ alkyl. In another embodiment, $R_1$ is —C(O)N(R$_4$)$_2$, and each $R_4$ is independently linear or branched $C_1$ to $C_4$ alkyl. In another embodiment, $R_6$ is $C_1$–$C_4$ alkyl, $R_1$ is —CO$_2$R$_3$, and at least one of $R_2$ and $R_3$ is linear or branched $C_8$ to $C_{20}$ alkyl. In yet another embodiment, $R_2$ and $R_3$ are each linear or branched $C_8$–$C_{12}$ alkyl. In another embodiment, $R_2$ and $R_3$ are linear or branched $C_{12}$ to $C_{20}$ alkyl. In yet another embodiment, $R_6$ is methyl or ethyl.

In another embodiment, the present invention relates to a sunscreen composition comprising i) at least one UV-A organic sunscreen and ii) at least one compound of formula VII or VIII

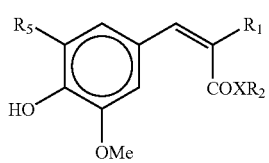

VII

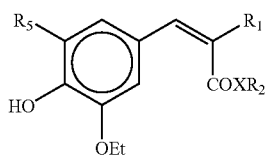

VIII wherein $R_1$ is selected from the group consisting —C(O)CH$_3$, —CO$_2$ (C$_1$–C$_8$ alkyl), —C(O)NH$_2$, —C(O)N(C$_1$–C$_4$ alkyl)$_2$, and —CN; X is O or NH; and $R_2$ is $C_1$–$C_{12}$ alkyl, and $R_5$ is $C_1$–$C_8$ linear or branched alkyl and said composition optionally contains at least one UV-B liquid organic sunscreen and/or at least one solubilizer.

In another embodiment the sunscreen composition of the invention is prepared by sol gel encapsulation.

In yet another embodiment, X of formula VII or VIII is oxygen and $R_2$ is linear or branched $C_1$ to $C_4$ alkyl. In another embodiment, $R_1$ is —CO$_2$C$_8$H$_{18}$.

In another embodiment the compound of formula V is selected from the group consisting of ethyl-alpha-cyano-3-methoxy-4-hydroxy cinnamate; ethyl-alpha-acetyl-3-methoxy-4-hydroxy cinnamate; iso-propyl-alpha-acetyl-3-methoxy-4-hydroxy cinnamate; iso-amyl-alpha-acetyl-3-methoxy-4-hydroxy cinnamate; 2-ethylhexyl-alpha-acetyl-3-methoxy-4-hydroxy cinnamate; diethyl-3-methoxy-4-hydroxy benzylidene malonate; di-(2-ethylhexyl)-3-methoxy-4-hydroxy benzylidene malonate; diisoamyl-3- methoxy-4-hydroxy benzylidene malonate; dipalmitoyl-3-methoxy-4-hydroxy benzylidene malonate; di-dodecyl-3-methoxy-4-hydroxy benzylidene malonate; di-isopropyl-3-methoxy-4-hydroxy benzylidene malonate; di-(2-ethyhexyl)-3-methoxy-4-hydroxy-5-isopropyl-benzylidene malonate; di-isoamyl-3-methoxy-4-hydroxy-5-tert.butyl-benzylidene malonate; iso-amyl-alpha-acetyl-3-methoxy-4-hydroxy-5-isopropyl cinnamate; and iso-amyl-alpha-acetyl-3-methoxy-4-hydroxy-5-tert.butyl cinnamate.

In another embodiment, the compound of formula V is present in an amount effective to adsorb illumination in a range from 290 to 400, preferably above 320 nm wavelength.

In one embodiment, the sunscreen composition comprises from 0.1 to 40 wt. % of a compound of formula V, and optionally contains an additional organic sunscreen agent for filtering UV-B rays, UV-A rays or both, said agent may be an inorganic metal oxide sunscreen agent. Preferably, the compound of Formula V stabilizes the additional sunscreen agent against degradation from exposure to light.

In another embodiment, the present invention relates to a personal care composition that comprises i) at least one UV-A organic sunscreen; ii) at least one compound of formula V.

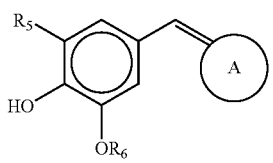

V wherein A is a moiety which is chromophoric within the UV radiation range of wavelengths to provide UV absorbing activity to the compound of formula I, wherein moiety A comprises one divalent group or two monovalent groups, with at least one group having carbonyl (C=O) functionality, $R_6$ is independently linear or branched $C_1$–$C_8$ alkyl, and $R_5$ is hydrogen or linear or branched $C_1$–$C_8$ alkyl; iii) at least one UV-B liquid organic sunscreen; iv) at least one solubilizer; v) a cosmetically acceptable carrier; and vi) at least one cosmetic adjuvant selected from the group consisting of preservatives, antifoams, perfumes, oils, waxes, propellants, dyes, pigments, waterproofing agents, emulsifiers, surfactants, thickeners, humectants, exfoliants and emollients, wherein said compound of formula V is present in an amount effective to absorb illumination in a range above 320 nm wavelength.

In another embodiment, the personal care composition is in a form selected from the group consisting of creams, ointment, suspensions, powders, oily lotions, oleo-alcoholic lotions, fatty gels, oleo-alcoholic gels, solid sticks, foams, emulsions, liquid dispersions, sprays and aerosols.

In yet another embodiment, the sunscreen composition is free of photostabilizers other than compounds of formula V, which is present in an amount within the range of 0.1% to 40 wt % of said sunscreen formulation.

In another embodiment, the sunscreen composition comprises an antioxidant other than a compound of formula V, said additional antioxidant may be, for example, Tocopherols, tocopherylacetate, Ascorbic acid, Emblica antioxidants, Proanthocyanidins, Rosemary antioxidants, green tea polyphenols, gallic acid, ellagic acid, butylhydroxy toluene (BHT) and butylhydroxy anisole (BHA).

In yet another embodiment, the compound of formula V is present in an amount effective to protect formulation ingredients from oxidation.

In another embodiment, the personal care composition is in the form of lipsticks, foundation, make-up, loose or press powder, eye blush, eye shadows or nail lacquer.

In yet another embodiment, the present invention relates to a method of protecting a substrate from UV radiation which comprises applying a sunscreen composition of the invention to said substrate.

The entire disclosure of all applications, patents and publications, cited herein are hereby incorporated by reference.

BRIEF DESCRIPTION OF THE DRAWINGS

FIG. 4 depicts a bar graph showing the photostabilization of Avobenzone in the presence of Octyl methoxycinnamte (OMC) with Oxynex® ST and TQ in formulated products.

EXAMPLES

EXAMPLE I

2-Ethylhexyl-alpha-aceto-3,5-dimethoxy-4-hydroxy cinnamate

Figure 1:
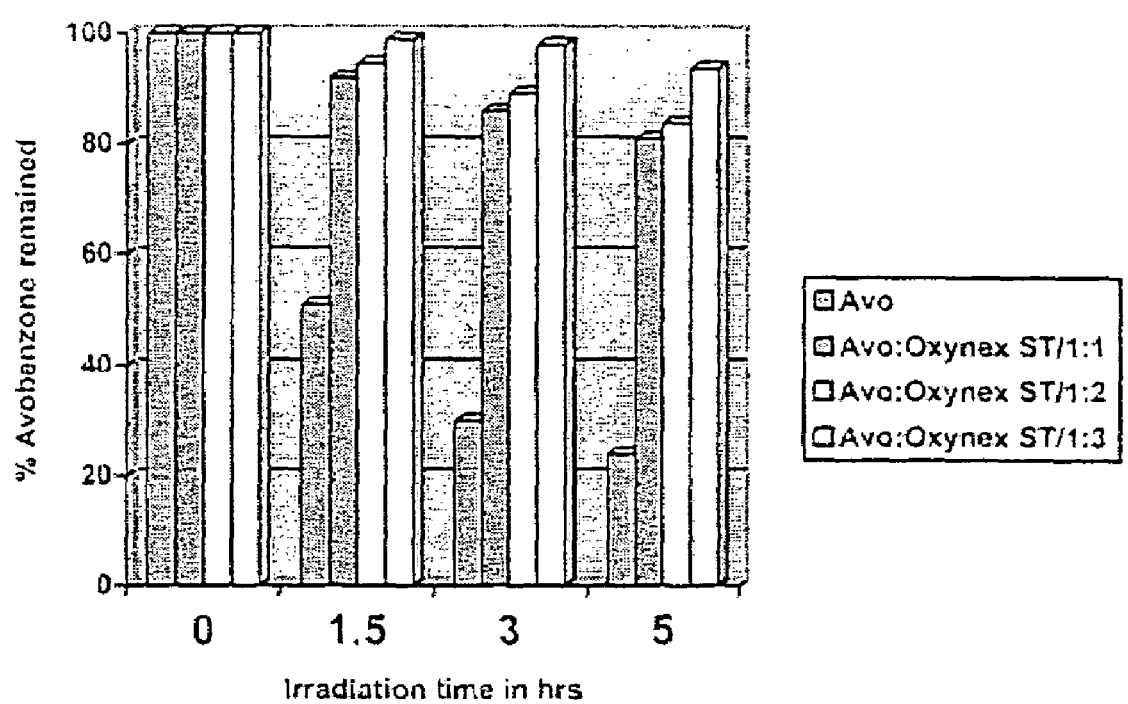
FIG. 1 depicts a bar graph showing the photostabilization of Avobenzone with Oxynex® ST in formulated products at different ratios.

Monodemethylation of 3,4,5-trimethoxy benzaldehyde using sulphuric acid at 40 ° C. for 8 hours yields 3,5-Dimethoxy-4-hydroxy benzaldehyde (Syringaldehyde). Condensation of syringaldehyde with 2-ethylhexyl acetoacetate in the presence of piperidine-acetic acid and benzene as the reaction medium at reflux temperature under continuous azeotropic water removal yields the title product. The reaction takes about 1.5 hours for completion. The yield obtained is typically 92%.

EXAMPLE II

Diethyl-3,5-dimethoxy-4-hydroxy benzylidene malonate

Monodemethylation of 3,4,5-trimethoxy benzaldehyde using sulphuric acid at 40° C. for 8 hours as described above in Example 1 yields syringaldehyde.

Condensation of 3,5-Dimethoxy-4-hydroxy benzaldehyde (Syringaldehyde) with diethyl malonate in the presence of piperidine-acetic acid and benzene as the reaction medium at reflux temperature under continuous azeotropic water removal yields the title product. The reaction takes about 7.5 hours for completion.

EXAMPLE III

Ethyl-alpha-methyl-3,5-dimethoxy-4-hydroxy cinnamate

Monodemethylation of 3,4,5,-trimethoxy benzaldehyde using sulphuric acid at 40° C. for 8 hours as described above in Example 1 yields syringaldehyde.

The Wittig salt is prepared by reaction of triphenyl phosphine and ethyl-2-bromopropionate in benzene media at 70–75° C. for 8 hours and subsequent basification with 1N Sodium hydroxide to phenolphthalein end point at room temperature. Extraction with benzene, concentration of the benzene extract and the addition of petroleum ether (60–80° C.) yield triphenyl methyl carbethoxy methylene phosphorane as a solid product.

Condensation of 3,5-Dimethoxy-4-hydroxy benzaldehyde (Syringaldehyde) with triphenyl methyl carbethoxy methylene phosphorane is performed at reflux temperature in xylene for seven hours and after work up, yields the title compound.

EXAMPLE IV

Ethyl-alpha-acetyl-3,5-dimethoxy-4-hydroxy-cinnamate

Monodemethylation of 3,4,5-trimethoxy benzaldehyde using sulphuric acid at 40° C. for 8 hours as described above in Example 1 yields syringaldehyde.

Condensation of 3,5-Dimethoxy-4-hydroxy benzaldehyde (syringaldehyde) with ethyl acetoacetate in the presence of piperidine-acetic acid and benzene as the reaction medium at reflux temperature yields the title product. The reaction takes about 3.5 hours for completion.

EXAMPLE VI

Di-(2-Ethylhexyl)-3,5-dimethoxy-4-hydroxy benzylidene malonate

Monodemethylation of 3,4,5-trimethoxy benzaldehyde using sulphuric acid at 40° C. for 8 hours as described above in Example I yields syringaldehyde.

Transesterfication of diethyl malonate using 2-ethylhexyl alcohol in neat condition at 140–155 °C for 2 hours under nitrogen blanketing in the presence of sulphuric acid and after work up, followed by high vacuum distillation, yields di-6-ethylhexyl malonate.

Condensation of 3,5-Dimethoxy-4-hydroxy benzaldehyde (Syringaldehyde) with di-2-ethylhexyl malonate in the presence of piperidine-acetic acid and benzene as the reaction medium at reflux temperature under continuous azeotropic water removal yields di-2-ethylhexyl-3,5-dimethoxy-4-hydroxy benzylidene malonate. The reaction takes about nine hours for completion. The yield typically obtained is 91%.

EXAMPLE VII

Di-isoamyl-3,5-dimethoxy-4-hydroxy benzylidene malonate

Example VI was repeated, except in the condensation step, di-2-ethylhexyl malonate was replaced with di-isoamyl malonate. The yield typically obtained was over 90%.

EXAMPLE VIII

Di-isopropyl-3,5-dimethoxy-4-hydroxy benzylidene malonate

Example VI was repeated, except in the condensation step, di-2-ethylhexyl malonate was replaced with di-isopropyl malonate. The yield typically obtained was over 90%.

EXAMPLE IX

Di-dodecyl-3,5-dimethoxy-4-hydroxy benzylidene malonate

Example VI was repeated, except in the condensation step, di-2-ethylhexyl malonate was replaced with di-dodecyl malonate. The yield typically obtained was over 90%.

EXAMPLE X

Iso-propyl-alpha-acetyl-3,5-diimethoxy-4-hydroxy-cinnamate

Example IV was repeated, except in the condensation step, ethyl acetoacetate was replaced with iso-propyl acetoacetate. The yield of the desired product was 88%.

EXAMPLE XI

Iso-butyl-alpha-acetyl-3,5-dimethoxy-4-hydroxy-cinnamate

Example IV was repeated, except in the condensation step, ethylacetoacetate was replaced with iso-butyl-acetoacetate. The yield of the desired product was 89%.

EXAMPLE XII

Iso-amyl-alpha-acetyl-3,5-dimethoxy-4-hydroxy-cinnamate

Example IV was repeated, except in the condensation step, ethylacetoacetate was replaced with iso-amyl acetoacetate. The yield of the desired product was 89%.

EXAMPLE XIII

Ethyl-alpha-cyano-3-methoxy-4-hydroxy cinnamate

Condensation of vanillin with ethyl cyanoacetate in the presence of piperidine-acetic acid and benzene as the reaction medium at reflux temperature under continuous azeotropic water removal yields the title product. The reaction takes about 1.5 hours for completion. The yield obtained is typically 95%.

EXAMPLE XIV

Diethyl-3-methoxy-4-hydroxy benzylidene malonate

Condensation of 3-methoxy-4-hydroxy benzaldehyde (vanillin) with diethyl malonate in the presence of piperidine-acetic acid and benzene as the reaction medium at reflux temperature under continuous azeotropic water removal yields the title product. The reaction takes about 6.5 hours for completion.

EXAMPLE XV

Ethyl-alpha-acetyl-3-methoxy-4-hydroxy-cinnamate

Condensation of 3-methoxy-4-hydroxy benzaldehyde (vanillin) with ethyl acetoacetate in the presence of piperidine-acetic acid and benzene as the reaction medium at reflux temperature yields the title product. The reaction takes about 3.5 hours for completion.

EXAMPLE XVI

Di-(2-Ethylhexyl)-3-methoxy-4-hydroxy benzylidene malonate

Transesterification of diethyl malonate using 2-ethylhexyl alcohol in neat condition at 140–155° C. for 2 hours under nitrogen blanketing in the presence of sulfuric acid and after work up, followed by high vacuum distillation, yields di-6-ethylhexyl malonate.

Condensation of 3-methoxy-4-hydroxy benzaldehyde (vanillin) with di-2-ethylhexyl malonate in the presence of piperidine-acetic acid and benzene as the reaction medium at reflux temperature under continuous azeotropic water removal yields di-2-ethylhexyl-3-methoxy-4-hydroxy benzylidene malonate. The reaction takes about nine hours for completion. The yield typically obtained is 91%.

EXAMPLE XVII

Di-isoamyl-3-methoxy-4-hydroxy benzylidene malonate

EXAMPLE IV is repeated, except in the condensation step, di-2-ethyhexyl malonate is replaced with di-isoamyl malonate. The yield typically obtained is over 90%.

EXAMPLE XVIII

Di-isopropyl-3-ethoxy-4-hydroxy benzylidene malonate

Example IV is repeated, except in the condensation step, di-2-ethyhexyl malonate is replaced with di-isopropyl malonate. The yield typically obtained is over 90%.

EXAMPLE XIX

Di-dodecyl-3-methoxy-4-hydroxy benzylidene malonate

Example IV is repeated, except in the condensation step, di-2-ethyhexyl malonate is replaced with di-dodecyl malonate. The yield typically obtained is over 90%.

EXAMPLE XX

Iso-propyl-alpha-acetyl-3-methoxy-4-hydroxy-cinnamate

Example III is repeated, except in the condensation step, ethyl acetoacetate is replaced with iso-propyl acetoacetate. The yield of the desired product is 88%.

EXAMPLE XXI

Iso-butyl-alpha-acetyl-3-methoxy-4-hydroxy-cinnamate

Example III is repeated, except in the condensation step, ethylacetoacetate is replaced with iso-butyl-acetoacetate. The yield of the desired product is 89%.

EXAMPLE XXII

Iso-amyl-alpha-acetyl-3-methoxy-4-hydroxy-cinnamate

Example III is repeated, except in the condensation step, ethylacetoacetate is replaced with iso-amyl acetoacetate. The yield of the desired product is 89%.

EXAMPLE XXIII

Disoamyl-3-methoxy-4-hydroxy-5-isopropyl benzylidene malonate

Condensation of 3-methoxy-4-hydroxy-5-isopropyl benzaldehyde with di-isoamyl malonate in the presence of piperidine-acetic acid and benzene as the reaction medium at reflux temperature under continuous azeotropic water removal yields the title product. The reaction takes about 3 hours for completion. The yield obtained is typically 90–95%.

EXAMPLE XXIV

Isoamyl-alpha-acetyl-3-methoxy-4-hydroxy-5-isopropyl-cinnamate

Condensation of 3-methoxy-4-hydroxy-5-isopropyl benzaldehyde with isoamyl acetoacetate in the presence of piperidine-acetic acid and benzene as the reaction medium at reflux temperature under continuous azeotropic water removal yields the title product. The reaction takes about 4 hrs for completion. The yield obtained is typically 90–95%.

EXAMPLE XXV

This Example shows the effect of Oxynex® ST (Di-2-ethylhexyl-3,5-dimethoxy-4-hydroxy-benzalmalonate) on the photostability of Avobenzone. Oxynex® ST is a yellow viscous liquid having a $\lambda_{max}$ at 332 nm (MeOH, $\epsilon_{max}$ 18,600 cm$^{-1}$ mol$^{-1}$) or 337 nm (EtOH:H$_2$O/70:30, $\epsilon_{max}$ 19,840 cm$^{-1}$ mol$^{-1}$). It has an antioxidant activity (IC$_{50}$=85±8 µg/ml) as determined by the Diphenylpicryl Hydrazide (DPPH) test method.

DPPH Test Method

A DPPH concentrate (2.5×) of 25 mg of 1,1-Diphenyl-2-Picyrl-Hydrazyl ACS# 1898-66-4 (Sigma #D-9132, lot 99H$_{3601}$) dissolved in 250 mL ethanol (USP), is prepared fresh on the measurement date. A DPPH working solution is then prepared by diluting 100 mL of this concentrate to a final volume of 250 mL (100 µM/mL). A blank 13×100 mm borosilicate glass screw top tube of ethanol (USP) is used to zero the spectrometer (Milton Roy, Spectronic 20+) at 517 nm and a control tube of DPPH working solution is measured under identical conditions, and taken as 0% activity. Aliquots of the 0.25% & 0.5% (RT & 45° C.) test solution are added to tubes followed by the rapid addition of 4 mL DPPH working solution then rapidly capped and mixed. After 20 minutes, the absorbance of each sample is read at 517 nm.

The percent reducing activity (% RA) is calculated using the following equation:

$$\% \text{ Reduction Activity} = 100 \frac{A(0) - A(20)}{A(0)}$$

Where A(0) is the absorbance value of the DPPH working solution at 517 nm zeroed against an ethanol blank and A(20) is the absorbance at 517 nm, 20 minutes after combining the antioxidant with the DPPH working solution.

The concentration of antioxidant (mg/ml) in the final assay mixture is calculated based on the dilution of respective aliquots of each compound in the final assay volume and % RA tabulated and plotted as percent activity at each concentration in the dilution series.

Photostabilization of Avobenzone (in formulation) was performed using thin films (about 50–100 µ thick, transmission signals in the non-absorbing regions must be above 85%) of formulated materials placed between two glass slides and then irradiated under UV-B light (Q-U-V Accelerated Weather Tester, The Q Panel Company). Photodegradation of Avobenzone was calculated from the relative loss in absorption of Avobenzone in formulated products before and after irradiation. 1 hour irradiation under UV-B light is equal to about 1.4 MED (minimal erythemal dose). A Beckman Coulter DU-640 spectrophotometer at a scan speed of 120 nm/min was used for this study. All spectra were recorded from 200 to 600 nm. Effectiveness of Oxynex® ST was compared with Corapan TQ (Di-2-ethyl-hexyl-napthylate, H&R). Photostabilization of Avobenzone in HMS with Oxynex® ST or TQ in formulation was determined by using a ratio (w/w) of 2:6:2.

Figure 2:
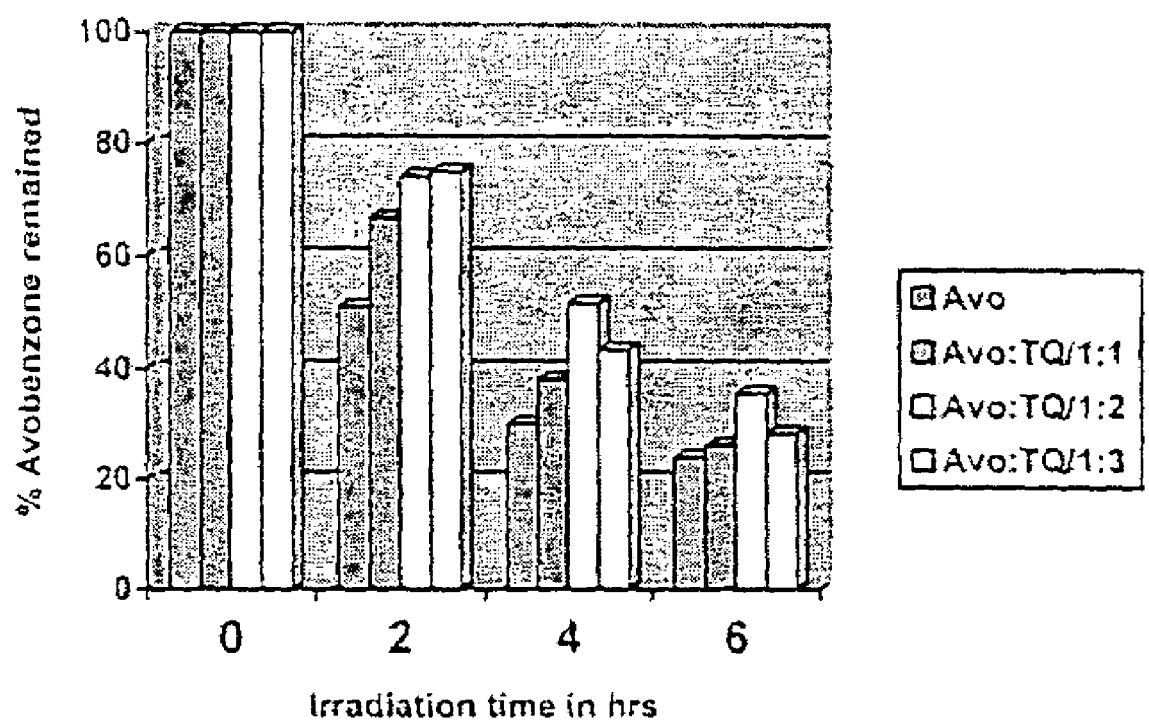
FIG. 2 depicts a bar graph showing the photostabilization of Avobenzone with Corapan TQ in formulated products at different ratios.
Figure 3:
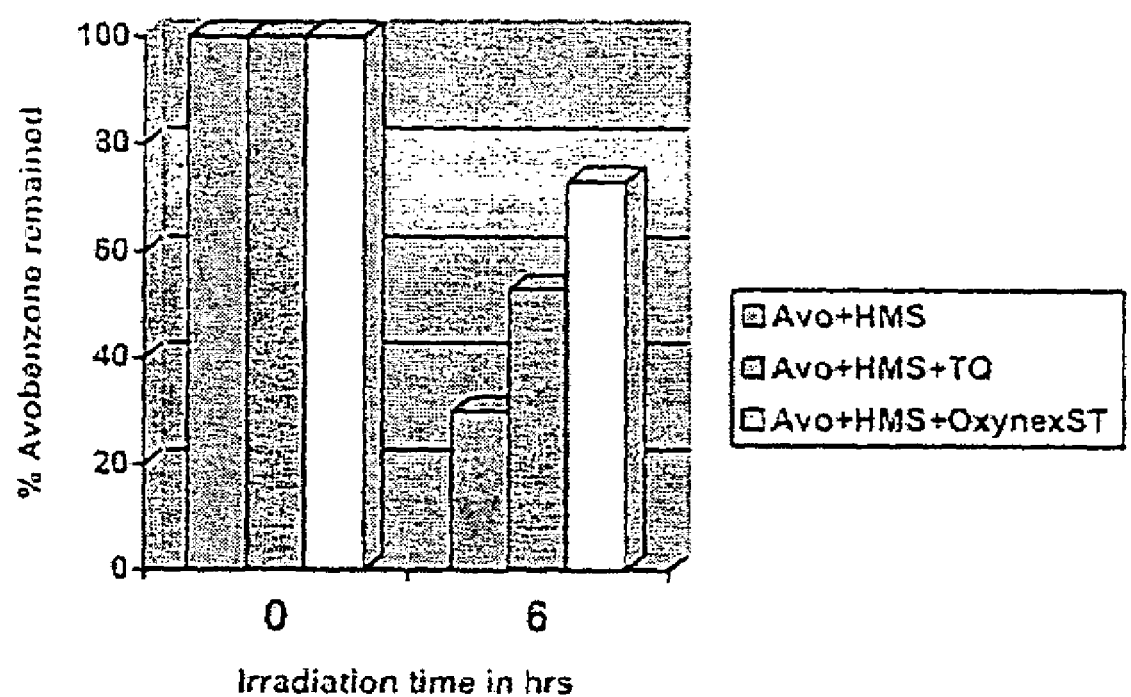
FIG. 3 depicts a bar graph showing the photostabilization of Avobenzone in the presence of Homosalate (HMS) with Oxynex® ST and TQ in formulated products. The critical wavelength (in nm) was 381 for Avo+HMS (2:6); Avo+HMS+TQ (2:6:2); and Avo+HMS+ST (2:6:2). The in vitro SPF was 27 for Avo+HMS (2:6); 30 for Avo+HMS+TQ (2:6:2); and 35 for Avo+HMS+ST (2:6:2).

A three fold (from 24% to 81%) increase in Avobenzone stability in the presence of Oxynex® ST photostabilizer (1:1, w/w) was observed (FIG. 1). Further improvement in Avobenzone stabilization was seen when Oxynex® ST was used at a 1:2 or 1:3 ratio. TQ, on the other hand, had practically no effect on the photostabilization of Avobenzone when used alone (FIG. 2). TQ also failed to stabilize Avobenzone when combined with Homosalate. However, the stabilization efficiency of Oxynex® ST on Avobenzone in the presence of HMS was about three-fold higher (from 14 to 566) (FIG. 3). Oxynex ST also improves the photostability of Avobenzone in the presence of OMC by two-fold (from 36% to 73%) (FIG. 4).

In vitro studies showed, Avobenzone (2%) in the presence of HMS (6%) and Oxynex® ST (2%) had the appropriate critical wavelength and SPF (>30).

The solubility of Avobenzone was tested in various ratios of Oxynex® ST and HMS. The results are summarized below.

TABLE I

Solubility of Avobenzone in the Oxynex® ST Photostabilizer + HMS

| Avobenzone | Oxynex® ST | HMS | Storage Temp | 24 hr | 1 week | 2 weeks | 3 weeks | 6 weeks |
|---|---|---|---|---|---|---|---|---|
| 15 | 15 | 70 | RT | Clear | Clear | Clear | Clear | Clear |
|  |  |  | 4° C. | Clear | Clear | Crystal? | Crystal? | Ppt |
| 20 | 20 | 60 | RT | Clear | Clear | Clear | Clear | Clear |
|  |  |  | 4° C. | Clear | Clear | Crystal? | Crystal? | Ppt |
| 25 | 25 | 50 | RT | Clear | Clear | Crystal? | Ppt | Ppt |
|  |  |  | 4° C. | Clear | Ppt | Ppt | Ppt | Ppt |
| 30 | 30 | 40 | RT | Clear | Ppt | Ppt | Ppt | Ppt |
|  |  |  | 4° C. | Clear | Ppt | Ppt | Ppt | Ppt |

Ppt = precipitate

Considering the solubility of Avobenzone in different rations of HMS and Oxynex® ST, the following ratios for encapsulation of Avobenzone (UV-Pearl Avo) using the Sol-Gel process are preferred: Avobenzone/Oxynex® ST/HMS: 20/20/60 and 25/25/50.

TABLE II

Solubility of Avobenzone in the Oxynex® ST Photostabilizer + OMC

| Avobenzone | Oxynex® ST | OMC | Storage Temp | 48 hr | 1 week | 2 weeks |
|---|---|---|---|---|---|---|
| 20 | 20 | 60 | RT | Clear | Clear | Clear |
|  |  |  | 4° C. | Clear | Clear | Crystal? |
| 25 | 25 | 50 | RT | Clear | Clear | Crystal? |
|  |  |  | 4° C. | Clear | Ppt | Ppt |
| 30 | 20 | 50 | RT | Few Crystals |  |  |
|  |  |  | 4° C. | Few Crystals |  |  |

Ppt = precipitate

Considering the solubility of Avobenzone in different rations of OMC and Oxynex® ST, the following ratios for encapsulation of Avobenzone (UV-Pearl Avo) using the Sol-Gel process are preferred: Avobenzone/Oxynex® ST/OMC: 20/20/60 and 25/25/50.

The preceding examples can be repeated with similar success by substituting the generically or specifically described reactants and/or operating conditions of this invention for those used in the examples.

From the foregoing description, one skilled in the art can easily ascertain the essential characteristics of this invention, and without departing from the spirit and scope thereof, can make various changes and modifications of the invention to adapt it to various usages and conditions.

What is claimed is:

1. A sunscreen composition comprising
i) at least one UV-A organic sunscreen selected from the group consisting of 2-Methyldibenzoylmethane, 4-Methyldibenzoylmethane, 4-Isopropyldibenzoylmethane, 4-Tert-butyldibenzoylmethane, 2,4-Dimethyldibenzoylmethane, 2,5-Dimethyldibenzoylmethane, 4,4'-Diisopropyldibenzoylmethane, 4,4'-Dimethyldibenzoylmethane, 4-Tert-butyl-4'-methoxydibenzoylmethane, 2-Methyl-5-isopropyl-4'-methoxydibenzoylmethane, 2-Methyl-5-tert-butyl-4'-methoxydibenzoylmethane, 2,4-Dimethyl-4'-methoxydibenzoylmethane, 2,6-Dimethyl-4-tert-butyl-4'-methoxydibenzoylmethane; and
ii) at least one compound of formula I or II

I

II wherein
A is a moiety which provides chromophoric properties;
each R is independently linear or branched $C_1$ to $C_8$ alkyl;
$R_1$ is selected from the group consisting of —C(O)CH$_3$, —CO$_2$R$_3$, —C(O)NH$_2$, —C(O)N(R$_4$)$_2$ and —CN;
X is O or NH;
$R_2$ is linear or branched $C_1$ to $C_{20}$ alkyl;
$R_3$ is linear or branched $C_1$ to $C_{20}$ alkyl; and
each $R_4$ is independently hydrogen or linear or branched $C_1$ to $C_8$ alkyl.

2. The sunscreen composition of claim 1, wherein said composition is prepared by sol gel encapsulation.

3. The sunscreen composition of claim 1, further comprising at least one UV-B liquid organic sunscreen.

4. The sunscreen composition of claim 3, wherein said composition is prepared by sol gel encapsulation.

5. The sunscreen composition of claim 1, further comprising at least one solubilizer.

6. The sunscreen composition of claim 5, wherein said composition is prepared by sol gel encapsulation.

7. The sunscreen composition of claim 1, further comprising at least one UV-B liquid organic sunscreen and at least one solubilizer.

8. The sunscreen composition of claim 7, wherein said composition is prepared by sol gel encapsulation.

9. A sunscreen composition comprising
i) at least one UV-A organic sunscreen selected from the group consisting of 2-Methyldibenzoylmethane, 4-Methyldibenzoylmethane, 4-Isopropyldibenzoylmethane, 4-Tert-butyldibenzoylmethane, 2,4-Dimethyldibenzoylmethane, 2,5-Dimethyldibenzoylmethane, 4,4'-Diisopropyldibenzoylmethane, 4,4'-Dimethyldibenzoylmethane, 4-Tert-butyl-4'-methoxydibenzoylmethane, 2-Methyl-5-isopropyl-4'-methoxydibenzoylmethane, 2-Methyl-5-tert-butyl-4'-methoxydibenzoylmethane, 2,4-Dimethyl-4'-methoxydibenzoylmethane, 2,6-Dimethyl-4-tert-butyl-4'-methoxydibenzoylmethane; and
ii) at least one compound of formula I or II

I

II wherein
A is a moiety which provides chromophoric properties;
each R is independently linear or branched $C_1$ to $C_8$ alkyl;
$R_1$ is selected from the group consisting —C(O)CH$_3$, —CO$_2$R$_3$, —C(O)NH$_2$ and —C(O)N(R$_4$)$_2$;
X is O or NH;
$R_2$ is linear or branched $C_1$ to $C_{20}$ alkyl;
$R_3$ is linear or branched $C_1$ to $C_{20}$ alkyl; and
each $R_4$ is independently hydrogen or linear or branched $C_1$ to $C_8$ alkyl.

10. The sunscreen composition of claim 9, wherein said composition is prepared by sol gel encapsulation.

11. The sunscreen composition of claim 9, further comprising at least one UV-B liquid organic sunscreen.

12. The sunscreen composition of claim 11, wherein said composition is prepared by sol gel encapsulation.

13. The sunscreen composition of claim 9, further comprising at least one solubilizer.

14. The sunscreen composition of claim 13, wherein said composition is prepared by sol gel encapsulation.

15. The sunscreen composition of claim 9, further comprising at least one UV-B liquid organic sunscreen and at least one solubilizer.

16. The sunscreen composition of claim 15, wherein said composition is prepared by sol gel encapsulation.

17. A composition of claim 9 wherein R is $C_1$–$C_4$ alkyl, X is oxygen and $R_2$ is linear or branched $C_1$ to $C_4$ alkyl.

18. A composition of claim 17 wherein $R_1$ is CO$_2$R$_3$ and, $R_3$ is linear or branched $C_1$ to $C_4$ alkyl.

19. A composition of claim 17 wherein $R_1$ is C(O)CH$_3$.

20. A composition of claim 17 wherein $R_1$ is —C(O)N(R$_4$)$_2$, and at least one $R_4$ is hydrogen and the other is hydrogen or linear or branched $C_1$ to $C_4$ alkyl.

21. A composition of claim 17 wherein $R_1$ is —C(O)N$(R_4)_2$, and each $R_4$ is independently linear or branched $C_1$ to $C_4$ alkyl.

22. A composition of claim 9 wherein R is $C_1$–$C_4$ alkyl, $R_1$ is —CO$_2$R$_3$, and at least one of $R_2$ and $R_3$ is linear or branched $C_8$ to $C_{20}$ alkyl.

23. A composition of claim 22 wherein $R_2$ and $R_3$ are each linear or branched $C_8$ alkyl.

24. A composition of claim 22 wherein at least one of $R_2$ and $R_3$ is linear or branched $C_{12}$ to $C_{20}$ alkyl.

25. A composition as in claim 9 wherein R is methyl or ethyl.

26. A sunscreen composition comprising
   i) at least one UV-A organic sunscreen selected from the group consisting of 2-Methyldibenzoylmethane, 4-Methyldibenzoylmethane, 4-Isopropyldibenzoylmethane, 4-Tert-butyldibenzoylmethane, 2,4-Dimethyldibenzoylmethane, 2,5-Dimethyldibenzoylmethane, 4,4'-Diisopropyldibenzoylmethane, 4,4'-Dimethyldibenzoylmethane, 4-Tert-butyl-4'-methoxydibenzoylmethane, 2-Methyl-5-isopropyl-4'-methoxydibenzoylmethane, 2-Methyl-5-tert-butyl-4'-methoxydibenzoylmethane, 2,4-Dimethyl-4'-methoxydibenzoylmethane, 2,6-Dimethyl-4-tert-butyl-4'-methoxydibenzoylmethane; and
   ii) at least one compound of formula III or IV

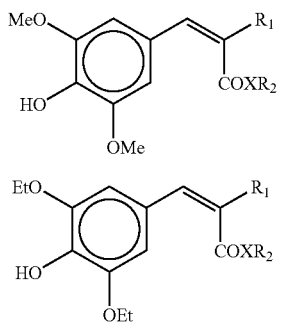

wherein
   $R_1$ is selected from the group consisting —C(O)CH$_3$, —CO$_2$ ($C_1$–$C_8$ alkyl), —C(O)NH$_2$, —C(O)N($C_1$–$C_4$ alkyl)$_2$ and —CN;
   X is O or NH; and
   $R_2$ is $C_1$–$C_{12}$ alkyl.

27. The sunscreen composition of claim 26, wherein said composition is prepared by sol gel encapsulation.

28. The sunscreen composition of claim 26, further comprising at least one UV-B liquid organic sunscreen.

29. The sunscreen composition of claim 28, wherein said composition is prepared by sol gel encapsulation.

30. The sunscreen composition of claim 26, further comprising at least one solubilizer.

31. The sunscreen composition of claim 30, wherein said composition is prepared by sol gel encapsulation.

32. The sunscreen composition of claim 26, further comprising at least one UV-B liquid organic sunscreen and at least one solubilizer.

33. The sunscreen composition of claim 32, wherein said composition is prepared by sol gel encapsulation.

34. A sunscreen composition comprising
   i) at least one UV-A organic sunscreen selected from the group consisting of 2-Methyldibenzoylmethane, 4-Methyldibenzoylmethane, 4-Isopropyldibenzoylmethane, 4-Tert-butyldibenzoylmethane, 2,4-Dimethyldibenzoylmethane, 2,5-Dimethyldibenzoylmethane, 4,4'-Diisopropyldibenzoylmethane, 4,4'-Dimethyldibenzoylmethane, 4-Tert-butyl-4'-methoxydibenzoylmethane, 2-Methyl-5-isopropyl-4'-methoxydibenzoylmethane, 2-Methyl-5-tert-butyl-4'-methoxydibenzoylmethane, 2,4-Dimethyl-4'-methoxydibenzoylmethane, 2,6-Dimethyl-4-tert-butyl-4'-methoxydibenzoylmethane; and
   ii) at least one compound of formula III or IV

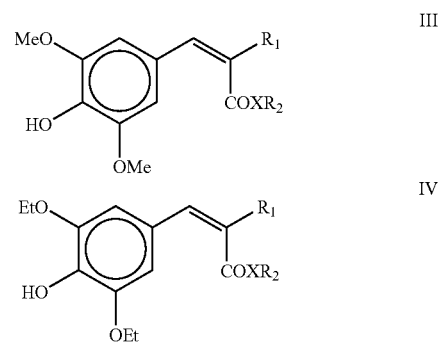

wherein
   $R_1$ is selected from the group consisting —C(O)CH$_3$, —CO$_2$ ($C_1$–$C_8$ alkyl), —C(O)NH$_2$, —C(O)NH ($C_1$–$C_4$ alkyl), and —C(O)N($C_1$–$C_4$ alkyl)$_2$;
   X is O or NH; and
   $R_2$ is $C_1$–$C_{12}$ alkyl.

35. The sunscreen composition of claim 34, wherein said composition is prepared by sol gel encapsulation.

36. The sunscreen composition of claim 34, further comprising at least one UV-B liquid organic sunscreen.

37. The sunscreen composition of claim 36, wherein said composition is prepared by sol gel encapsulation.

38. The sunscreen composition of claim 34, further comprising at least one solubilizer.

39. The sunscreen composition of claim 38, wherein said composition is prepared by sol gel encapsulation.

40. The sunscreen composition of claim 34, further comprising at least one UV-B liquid organic sunscreen and at least one solubilizer.

41. The sunscreen composition of claim 40, wherein said composition is prepared by sol gel encapsulation.

42. A composition of claim 34 wherein X is oxygen and $R_2$ is linear or branched $C_1$ to $C_4$ alkyl and $R_1$ is selected from the group consisting of —CO$_2$($C_1$–$C_4$ alkyl); —C(O)NH($C_1$–$C_4$ alkyl), —C(O)CH$_3$, —C(O)NH$_2$, and —C(O)N($C_1$–$C_4$ alkyl)$_2$.

43. A composition of claim 34 wherein $R_1$ is —CO$_2$C$_8$H$_{18}$.

44. A composition of claim 9 wherein said compound of formula II is selected from the group consisting of
   ethyl-alpha-acetyl-3,5-dimethoxy-4-hydroxy cinnamate,
   iso-propyl-alpha-acetyl-3,5-dimethoxy-4-hydroxy cinnamate,
   iso-amyl-alpha-acetyl-3,5-dimethoxy-4-hydroxy cinnamate,
   2-ethylhexyl-alpha-acetyl-3,5-dimethoxy-4-hydroxy cinnamate,
   diethyl-3,5-dimethoxy-4-hydroxy benzylidene malonate,
   di-(2-ethylhexyl)-3,5-dimethoxy-4-hydroxy benzylidene malonate, diisoamyl-3,5-dimethoxy-4-hydroxy benzylidene malonate, dipalmitoyl-3,5-dimethoxy-4-hydroxy benzylidene malonate, di-dodecyl-3,5-dimethoxy-4-hydroxy benzylidene malonate, and di-isopropyl-3,5-dimethoxy-4-hydroxy benzylidene malonate.

45. A sunscreen composition of claim 9 wherein said compound of formula II is present in an amount effective to adsorb illumination in a range above 320 nm wavelength.

46. A sunscreen composition of claim 9 wherein said compound of formula II is present in an amount effective to adsorb illumination in a range from 290 to 400 nm wavelength.

47. A sunscreen composition of claim 45, which comprises from 0.1 to 40 wt. % of a compound of formula II.

48. A sunscreen composition of claim 45 comprising an additional organic sunscreen agent for filtering UV-B rays, UV-A rays or both.

49. A sunscreen composition of claim 48, wherein the compound of Formula It stabilizes the additional sunscreen agent against degradation from exposure to light.

50. A sunscreen composition of claim 47, which additionally comprises an inorganic metal oxide sunscreen agent.

51. A personal care composition that comprises
i) at least one UV-A organic sunscreen selected from the group consisting of 2-Methyldibenzoylmethane, 4-Methyldibenzoylmethane, 4-Isopropyldibenzoylmethane, 4-Tert-butyldibenzoylmethane, 2,4-Dimethyldibenzoylmethane, 2,5-Dimethyldibenzoylmethane, 4,4'-Di-isopropyldibenzoylmethane, 4,4'-Dimethyldibenzoylmethane, 4-Tert-butyl-4'-methoxydibenzoylmethane, 2-Methyl-5-isopropyl-4'-methoxydibenzoylmethane, 2-Methyl-5-tert-butyl-4'-methoxydibenzoylmethane, 2,4-Dimethyl-4'-methoxydibenzoylmethane, 2,6-Dimethyl-4-tert-butyl-4'-methoxydibenzoylmethane;
ii) at least one compound of formula I or II

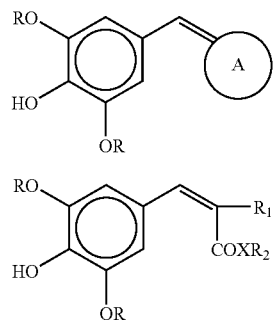

wherein
A is a moiety which provides chromophoric properties;
each R is independently linear or branched $C_1$ to $C_8$ alkyl;
$R_1$ is selected from the group consisting —C(O)CH$_3$, —CO$_2$R$_3$, —C(O)NH$_2$ and —C(O)N(R$_4$)$_2$;
X is O or NH;
$R_2$ is linear or branched $C_1$ to $C_{20}$ alkyl;
$R_3$ is linear or branched $C_1$ to $C_{20}$ alkyl; and
each $R_4$ is independently hydrogen or linear or branched $C_1$ to $C_8$ alkyl;

iii) at least one UV-B liquid organic sunscreen;
iv) at least one solubilizer,
v) a cosmetically acceptable carrier; and
vi) at least one cosmetic adjuvant selected from the group consisting of preservatives, antifoams, perfumes, oils, waxes, propellants, dyes, pigments, waterproofing agents, emulsifiers, surfactants, thickeners, humectants, exfoliants and emollients, wherein said a compound of formula II is present in an amount effective to absorb illumination in a range above 320 nm wavelength.

52. A personal care composition of claim 51 which is in a form selected from the group consisting of creams, ointment, suspensions, powders, oily lotions, oleo-alcoholic lotions, fatty gels, oleo-alcoholic gels, solid sticks, foams, emulsions, liquid dispersions, sprays and aerosols.

53. A method of protecting a substrate from UV radiation comprising applying a sunscreen composition of claim 45 to said substrate.

54. A method of protecting a substrate of skin or hair from UV radiation comprising applying a personal care composition of claim 51 to said substrate of skin or hair.

55. A method of claim 54 wherein the personal care composition additionally comprises an antioxidant selected from the group consisting of tocopherols, tocopherylacetate, Ascorbic acid, Emblica antioxidants, Proanthocyanidins, Rosemary antioxidants, green tea polyphenols, gallic acid, ellagic acid, butylhydroxy toluene (BHT) and butylhydroxy anisole (BHA).

56. A personal care composition of claim 51 further comprising an antioxidant other than a compound of formula I or II.

57. A personal care composition of claim 56 wherein the antioxidant is selected from the group consisting of Tocopherols, tocopherylacetate, Ascorbic acid, Emblica antioxidants, Proanthocyanidins, Rosemary antioxidants, green tea polyphenols, gallic acid, ellagic acid, butylhydroxy toluene (BHT) and butylhydroxy anisole (BHA).

58. A personal care composition of claim 51, wherein said compound of formula II is present in an amount effective to protect composition ingredients from oxidation.

59. A personal care composition of claim 58 in the form of lipsticks, foundation, make-up, loose or press powder, eye blush, eye shadows or nail lacquer.

60. A sunscreen care composition of claim 9, wherein said compound of formula II is present in an amount effective to absorb illumination in a range above 320 nm wavelength, said composition further comprises a cosmetically acceptable carrier and at least one cosmetic adjuvant selected from the group consisting of preservatives, antifoams, perfumes, oils, waxes, propellants, dyes, pigments, waterproofing agents, emulsifiers, surfactants, thickeners, humectants, exfoliants and emollients, and said composition is in a form selected from the group consisting of creams, ointment, suspensions, powders, oily lotions, oleo-alcoholic lotions, fatty gels, oleo-alcoholic gels, solid sticks, foams, emulsions, liquid dispersions, sprays and aerosols.

61. A sunscreen composition comprising
i) at least one UV-A organic sunscreen selected from the group consisting of 2-Methyldibenzoylmethane, 4-Methyldibenzoylmethane, 4-Isopropyldibenzoylmethane, 4-Tert-butyldibenzoylmethane, 2,4-Dimethyldibenzoylmethane, 2,5-Dimethyldibenzoylmethane, 4,4'-Di-isopropyldibenzoylmethane, 4,4'-Dimethyldibenzoylmethane, 4-Tert-butyl-4'-methoxydibenzoylmethane, 2-Methyl-5-isopropyl-4'-methoxydibenzoylmethane, 2-Methyl-5-tert-butyl-4'-methoxydibenzoylmethane, 2,4-Dimethyl-4'-methoxydibenzoylmethane, 2,6-Dimethyl-4-tert-butyl-4'-methoxydibenzoylmethane; and ii) at least one compound selected from the group consisting of ethyl-alpha-acetyl-3,5-dimethoxy-4-hydroxy cinnamate, iso-propyl-alpha-acetyl-3,5-dimethoxy-4-hydroxy cinnamate, iso-amyl-alpha-acetyl-3,5-dimethoxy-4-hydroxy cinnamate, 2-ethylhexyl-alpha-acetyl-3,5-dimethoxy-4-hydroxy cinnamate, diethyl-3,5-dimethoxy-4-hydroxy benzylidene malonate, di-(2-ethylhexyl)-3,5-dimethoxy-4-hydroxy benzylidene malonate, diisoamyl-3,5-dimethoxy-4-hydroxy benzylidene malonate, dipalmitoyl-3,5-dimethoxy-4-hydroxy benzylidene malonate, di-dodecyl-3,5-dimethoxy-4-hydroxy benzylidene malonate, and di-isopropyl-3,5-dimethoxy-4-hydroxy benzylidene malonate.

62. The sunscreen composition of claim 61, wherein said composition is prepared by sol gel encapsulation.

63. The sunscreen composition of claim 61, further comprising at least one UV-B liquid organic sunscreen.

64. The sunscreen composition of claim 63, wherein said composition is prepared by sol gel encapsulation.

65. The sunscreen composition of claim 61, further comprising at least one solubilizer.

66. The sunscreen composition of claim 65, wherein said composition is prepared by sol gel encapsulation.

67. The sunscreen composition of claim 61, further comprising at least one UV-B liquid organic sunscreen and at least one solubilizer.

68. The sunscreen composition of claim 67, wherein said composition is prepared by sol gel encapsulation.

69. A sunscreen composition of claim 9 further comprising an antioxidant other than a compound of formula I or II.

70. A sunscreen composition of claim 69 wherein the antioxidant is selected from the group consisting of Tocopherols, tocopherylacetate, Ascorbic acid, Emblica antioxidants, Proanthocyanidins, Rosemary antioxidants, green tea polyphenols, gallic acid, ellagic acid, butylhydroxy toluene (BHT) and butylhydroxy anisole (BHA).

71. A sunscreen composition of claim 9, wherein said UV-A organic sunscreen is 4-(tert-butyl)-4'-methoxydibenzoylmethane and said photostabilizer is di-2-ethylhexyl-3,5-dimethoxy-4-hydroxy-benzalmalonate.

72. A sunscreen composition of claim 71, wherein said 4-(tert-butyl)-4'-methoxydibenzoylmethane and di-2-ethylhexyl-3,5-dimethoxy-4-hydroxy-benzalmalonate are in a ratio of 1:2 or 1:3.

73. A sunscreen composition of claim 9, wherein said UV-A organic sunscreen is 4-(tert-butyl)-4'-methoxydibenzoylmethane and said photostabilizer is di-2-ethylhexyl-3,5 dimethoxy-4-hydroxy-benzalmalonate and Homosalate.

74. A sunscreen composition comprising
i) at least one UV-A organic sunscreen selected from the group consisting of 2-Methyldibenzoylmethane, 4-Methyldibenzoylmethane, 4-Isopropyldibenzoylmethane, 4-Tert-butyldibenzoylmethane, 2,4-Dimethyldibenzoylmethane, 2,5-Dimethyldibenzoylmethane, 4,4'-Diisopropyldibenzoylmethane, 4,4'-Dimethyldibenzoylmethane, 4-Tert-butyl-4'-methoxydibenzoylmethane, 2-Methyl-5-isopropyl-4'-methoxydibenzoylmethane, 2-Methyl-5-tert-butyl-4'-methoxydibenzoylmethane, 2,4-Dimethyl-4'-methoxydibenzoylmethane, 2,6-Dimethyl-4-tert-butyl-4'-methoxydibenzoylmethane; and ii) at least one compound of formula V

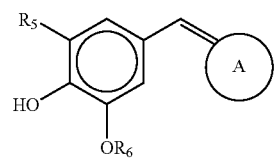

wherein
A is a moiety which is chromophoric within the UV radiation range of wavelengths to provide UV absorbing activity to the compound of formula I, wherein moiety A comprises one divalent group or two monovalent groups, with at least one group having carbonyl (C=O) functionality,
$R_6$ is independently linear or branched $C_1$–$C_8$ alkyl, and
$R_5$ is hydrogen or linear or branched $C_1$–$C_8$ alkyl.

75. The sunscreen composition of claim 74, wherein said composition is prepared by sol gel encapsulation.

76. The sunscreen composition of claim 74, further comprising at least one UV-B liquid organic sunscreen.

77. The sunscreen composition of claim 76, wherein said composition is prepared by sol gel encapsulation.

78. The sunscreen composition of claim 74, further comprising at least one solubilizer.

79. The sunscreen composition of claim 78, wherein said composition is prepared by sol gel encapsulation.

80. The sunscreen composition of claim 74, further comprising at least one UV-B liquid organic sunscreen and at least one solubilizer.

81. The sunscreen composition of claim 80, wherein said composition is prepared by sol gel encapsulation.

82. A sunscreen composition comprising
i) at least one UV-A organic sunscreen selected from the group consisting of 2-Methyldibenzoylmethane, 4-Methyldibenzoylmethane, 4-Isopropyldibenzoylmethane, 4-Tert-butyldibenzoylmethane, 2,4-Dimethyldibenzoylmethane, 2,5-Dimethyldibenzoylmethane, 4,4'-Diisopropyldibenzoylmethane, 4,4'-Dimethyldibenzoylmethane, 4-Tert-butyl-4'-methoxydibenzoylmethane, 2-Methyl-5-isopropyl-4'-methoxydibenzoylmethane, 2-Methyl-5-tert-butyl-4'-methoxydibenzoylmethane, 2,4-Dimethyl-4'-methoxydibenzoylmethane, 2,6-Dimethyl-4-tert-butyl-4'-methoxydibenzoylmethane; and ii) at least one compound of formula VI

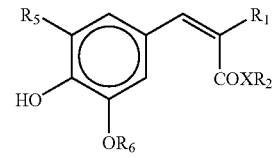

wherein
$R_1$ is selected from the group consisting of —C(O)CH$_3$, —CO$_2$R$_3$, —C(O)NH$_2$, —C(O)N(R$_4$)$_2$, and —CN;
X is O or NH;
$R_2$ is linear or branched $C_1$ to $C_{30}$ alkyl;
$R_3$ is linear or branched $C_1$ to $C_{20}$ alkyl; and
each $R_4$ is independently hydrogen, or linear or branched $C_1$ to $C_8$ alkyl;

$R_5$ is linear or branched $C_1$–$C_8$ alkyl or hydrogen,
and $R_6$ is $C_1$ to $C_8$ alkyl.

83. The sunscreen composition of claim 82, wherein said composition is prepared by sol gel encapsulation.

84. The sunscreen composition of claim 82, further comprising at least one UV-B liquid organic sunscreen.

85. The sunscreen composition of claim 84, wherein said composition is prepared by sol gel encapsulation.

86. The sunscreen composition of claim 82, further comprising at least one solubilizer.

87. The sunscreen composition of claim 86, wherein said composition is prepared by sol gel encapsulation.

88. The sunscreen composition of claim 82, further comprising at least one UV-B liquid organic sunscreen and at least one solubilizer.

89. The sunscreen composition of claim 88, wherein said composition is prepared by sol gel encapsulation.

90. The sunscreen composition of claim 82 wherein $R_6$ is $C_1$–$C_8$ alkyl, X is oxygen and $R_2$ is linear or branched $C_1$ to $C_4$ alkyl.

91. The sunscreen composition of claim 90 wherein $R_1$ is $CO_2R_3$ and, $R_3$ is linear or branched $C_1$ to $C_8$ alkyl.

92. The sunscreen composition of claim 90 wherein $R_1$ is $C(O)CH_3$.

93. The sunscreen composition of claim 90 wherein $R_1$ is —$C(O)N(R_4)_2$, and at least one $R_4$ is hydrogen and the other is hydrogen or linear or branched $C_1$ to $C_4$ alkyl.

94. The sunscreen composition of claim 90 wherein $R_1$ is —$C(O)N(R_4)_2$, and each $R_4$ is independently linear or branched $C_1$ to $C_4$ alkyl.

95. The sunscreen composition of claim 82 wherein $R_6$ is $C_1$–$C_4$ alkyl, $R_1$ is —$CO_2R_3$, and at least one of $R_2$ and $R_3$ is linear or branched $C_8$ to $C_{20}$ alkyl.

96. The sunscreen composition of claim 95 wherein $R_2$ and $R_3$ are each linear or branched $C_8$–$C_{12}$ alkyl.

97. The sunscreen composition of claim 95 wherein at least one of $R_2$ and $R_3$ is linear or branched $C_{12}$ to $C_{20}$ alkyl.

98. The sunscreen composition of claim 74 wherein $R_6$ is methyl or ethyl.

99. A sunscreen composition comprising
i) at least one UV-A organic sunscreen selected from the group consisting of 2-Methyldibenzoylmethane, 4-Methyldibenzoylmethane, 4-Isopropyldibenzoylmethane, 4-Tert-butyldibenzoylmethane, 2,4-Dimethyldibenzoylmethane, 2,5-Dimethyldibenzoylmethane, 4,4'-Diisopropyldibenzoylmethane, 4,4'-Dimethyldibenzoylmethane, 4-Tert-butyl-4'-methoxydibenzoylmethane, 2-Methyl-5-isopropyl-4'-methoxydibenzoylmethane, 2-Methyl-5-tert-butyl-4'-methoxydibenzoylmethane, 2,4-Dimethyl-4'-methoxydibenzoylmethane, 2,6-Dimethyl-4-tert-butyl-4'-methoxydibenzoylmethane; and
ii) at least one compound of formula VII or VIII

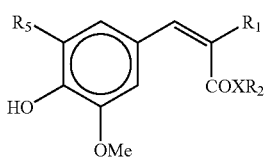

VII

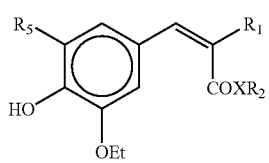

VIII wherein
$R_1$ is selected from the group consisting —$C(O)CH_3$, —$CO_2$ ($C_1$–$C_8$ alkyl), —$C(O)NH_2$, —$C(O)N(C_1$–$C_4$ alkyl)$_2$, and —CN;
X is O or NH; and
$R_2$ is $C_1$–$C_{12}$ alkyl, and
$R_5$ is $C_1$–$C_8$ linear or branched alkyl.

100. The sunscreen composition of claim 99, wherein said composition is prepared by sol gel encapsulation.

101. The sunscreen composition of claim 99, further comprising at least one UV-B liquid organic sunscreen.

102. The sunscreen composition of claim 101, wherein said composition is prepared by sol gel encapsulation.

103. The sunscreen composition of claim 99, further comprising at least one solubilizer.

104. The sunscreen composition of claim 103, wherein said composition is prepared by sol gel encapsulation.

105. The sunscreen composition of claim 99, further comprising at least one UV-B liquid organic sunscreen and at least one solubilizer.

106. The sunscreen composition of claim 105, wherein said composition is prepared by sol gel encapsulation.

107. The sunscreen composition of claim 99 wherein X is oxygen and $R_2$ is linear or branched $C_1$ to $C_4$ alkyl.

108. The sunscreen composition of claim 99 wherein $R_1$ is —$CO_2C_8H_{18}$.

109. The sunscreen composition of claim 74 wherein said compound of formula V is selected from the group consisting of
ethyl-alpha-cyano-3-methoxy-4-hydroxy cinnamate,
ethyl-alpha-acetyl-3-methoxy-4-hydroxy cinnamate,
iso-propyl-alpha-acetyl-3-methoxy-4-hydroxy cinnamate,
iso-amyl-alpha-acetyl-3-methoxy-4-hydroxy cinnamate,
2-ethylhexyl-alpha-acetyl-3-methoxy-4-hydroxy cinnamate,
diethyl-3-methoxy-4-hydroxy benzylidene malonate,
di-(2-ethylhexyl)-3-methoxy-4-hydroxy benzylidene malonate,
diisoamyl-3-methoxy-4-hydroxy benzylidene malonate,
dipalmitoyl-3-methoxy-4-hydroxy benzylidene malonate,
di-dodecyl-3-methoxy-4-hydroxy benzylidene malonate,
di-isopropyl-3-methoxy-4-hydroxy benzylidene malonate,
di-(2-ethyhexyl)-3-methoxy-4-hydroxy-5-isopropyl-benzylidene malonate,
di-isoamyl-3-methoxy-4-hydroxy-5-tert.butyl-benzylidene malonate,
iso-amyl-alpha-acetyl-3-methoxy-4-hydroxy-5-isopropyl cinnamate, and
iso-amyl-alpha-acetyl-3-methoxy-4-hydroxy-5-tert.butyl cinnamate.

110. The sunscreen composition of claim 74 wherein said compound of formula V is present in an amount effective to absorb illumination in a range above 320 nm wavelength.

111. The sunscreen composition of claim 74 wherein said compound of formula V is present in an amount effective to absorb illumination in a range of 290 to 400 nm wavelength.

112. The sunscreen composition of claim 110, which comprises from 0.1 to 40 wt. % of a compound of formula V.

113. The sunscreen composition of claim 110 comprising an additional organic sunscreen agent for filtering UV-B, UV-A rays or both.

114. A sunscreen formulation as in claim 112 wherein the compound of Formula V stabilizes the additional sunscreen agent against degradation from exposure to light.

115. A sunscreen formulation as in claim 112, which additionally comprises an inorganic metal oxide sunscreen agent.

116. A personal care composition that comprises
i) at least one UV-A organic sunscreen selected from the group consisting of 2-Methyldibenzoylmethane, 4-Methyldibenzoylmethane, 4-Isopropyldibenzoylmethane, 4-Tert-butyldibenzoylmethane, 2,4-Dimethyldibenzoylmethane, 2,5-Dimethyldibenzoylmethane, 4,4'-Diisopropyldibenzoylmethane, 4,4'-Dimethyldibenzoylmethane, 4-Tert-butyl-4'-methoxydibenzoylmethane, 2-Methyl-5-isopropyl-4'-methoxydibenzoylmethane, 2-Methyl-5-tert-butyl-4'-methoxydibenzoylmethane, 2,4-Dimethyl-4'-methoxydibenzoylmethane, 2,6-Dimethyl-4-tert-butyl-4'-methoxydibenzoylmethane;
ii) at least one compound of formula V;

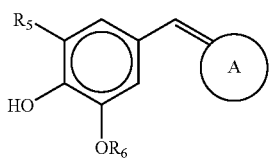

wherein
A is a moiety which is chromophoric within the UV radiation range of wavelengths to provide UV absorbing activity to the compound of formula I, wherein moiety A comprises one divalent group or two monovalent groups, with at least one group having carbonyl (C=O) functionality,
$R_6$ is independently linear or branched $C_1$–$C_8$ alkyl, and
$R_5$ is hydrogen or linear or branched $C_1$–$C_8$ alkyl
iii) at least one UV-B liquid organic sunscreen;
iv) at least one solubilizer;
v) a cosmetically acceptable carrier; and
vi) at least one cosmetic adjuvant selected from the group consisting of preservatives, antifoams, perfumes, oils, waxes, propellants, dyes, pigments, waterproofing agents, emulsifiers, surfactants, thickeners, humectants, exfoliants and emollients, wherein said compound of formula V is present in an amount effective to absorb illumination in a range above 320 nm wavelength.

117. A personal care composition of claim 116 which is in a form selected from the group consisting of creams, ointment, suspensions, powders, oily lotions, oleo-alcoholic lotions, fatty gels, oleo-alcoholic gels, solid sticks, foams, emulsions, liquid dispersions, sprays and aerosols.

118. A sunscreen composition of claim 113, which is free of photostabilizers other than compounds of formula V, which is present in an amount within the range of 0.1% to 40 wt % of said sunscreen formulation.

119. A method of protecting a substrate from UV radiation which comprises applying a sunscreen composition of claim 110 to said substrate.

120. A method as of protecting a substrate of skin or hair from UV radiation which comprises applying a personal care composition of claim 116 to a substrate of skin or hair.

121. A method as in claim 120 wherein the personal care composition additionally comprises an antioxidant selected from the group consisting of tocopherols, tocopherylacetate, Ascorbic acid, Emblica antioxidants, Proanthocyanidins, Rosemary antioxidants, green tea polyphenols, gallic acid, ellagic acid, butylhydroxy toluene (BHT) and butylhydroxy anisole (BHA).

122. A personal care composition of claim 116 further comprising an antioxidant other than a compound of formula V.

123. A personal care composition of claim 122 wherein the antioxidant is selected from the group consisting of Tocopherols, tocopherylacetate, Ascorbic acid, Emblica antioxidants, Proanthocyanidins, Rosemary antioxidants, green tea polyphenols, gallic acid, ellagic acid, butylhydroxy toluene (BHT) and butylhydroxy anisole (BHA).

124. A personal care composition of claim 116 wherein said compound of formula V is present in an amount effective to protect formulation ingredients from oxidation.

125. A personal care composition of claim 124, which is in the form of lipsticks, foundation, make-up, loose or press powder, eye blush, eye shadows or nail lacquer.

126. The sunscreen composition of claim 2, wherein said UV-A organic sunscreen is 4-(tert-butyl)-4'-methoxydibenzoylmethane.

127. The sunscreen composition of claim 10, wherein said UV-A organic sunscreen is 4-(tert-butyl)-4'-methoxydibenzoylmethane.

128. The sunscreen composition of claim 27, wherein said UV-A organic sunscreen is 4-(tert-butyl)-4'-methoxydibenzoylmethane.

129. The sunscreen composition of claim 35, wherein said UV-A organic sunscreen is 4-(tert-butyl)-4'-methoxydibenzoylmethane.

130. The personal care composition of claim 51, wherein the composition is prepared by sol gel encapsulation.

131. The sunscreen composition of claim 130, wherein said UV-A organic sunscreen is 4-(tert-butyl)-4'-methoxydibenzoylmethane.

132. The sunscreen composition of claim 75, wherein said UV-A organic sunscreen is 4-(tert-butyl)-4'-methoxydibenzoylmethane.

133. The sunscreen composition of claim 83, wherein said UV-A organic sunscreen is 4-(tert-butyl)-4'-methoxydibenzoylmethane.

134. The sunscreen composition of claim 100, wherein said UV-A organic sunscreen is 4-(tert-butyl)-4'-methoxydibenzoylmethane.

135. The personal care composition of claim 116, wherein the composition is prepared by sol gel encapsulation.

136. The sunscreen composition of claim 135, wherein said UV-A organic sunscreen is 4-(tert-butyl)-4'-methoxydibenzoylmethane.

* * * * *